US011339205B2

(12) United States Patent
Soucek et al.

(10) Patent No.: US 11,339,205 B2
(45) Date of Patent: *May 24, 2022

(54) METHODS AND COMPOSITIONS FOR THE TREATMENT OF CANCER

(71) Applicant: FUNDACIÓ PRIVADA INSTITUT D'INVESTIGACIÓ ONCOLÒGICA DE VALL HEBRON (FPIIOVH), Barcelona (ES)

(72) Inventors: Laura Soucek, Barcelona (ES); Marie-Eve Beaulieu, Barcelona (ES)

(73) Assignees: FUNDACIÓ PRIVADA INSTITUT D'INVESTIGACIÓ, Barcelona (ES); ONCOLÓGICA DE VALL HEBRON, Barcelona (ES)

(*) Notice: Subject to any disclaimer, the term of this patent is extended or adjusted under 35 U.S.C. 154(b) by 218 days.

This patent is subject to a terminal disclaimer.

(21) Appl. No.: 16/433,438

(22) Filed: Jun. 6, 2019

(65) Prior Publication Data

US 2019/0382468 A1 Dec. 19, 2019

Related U.S. Application Data

(63) Continuation of application No. 14/889,656, filed as application No. PCT/EP2014/059315 on May 7, 2014, now Pat. No. 10,370,434.

(30) Foreign Application Priority Data

May 7, 2013 (EP) ..................................... 13382167

(51) Int. Cl.
| | |
|---|---|
| *C07K 14/82* | (2006.01) |
| *A61K 45/06* | (2006.01) |
| *A61K 39/00* | (2006.01) |
| *A61K 38/08* | (2019.01) |
| *A61K 38/10* | (2006.01) |
| *C07K 7/06* | (2006.01) |
| *C07K 7/08* | (2006.01) |
| *A61K 38/00* | (2006.01) |

(52) U.S. Cl.
CPC .............. *C07K 14/82* (2013.01); *A61K 38/08* (2013.01); *A61K 38/10* (2013.01); *A61K 39/0011* (2013.01); *A61K 39/001152* (2018.08); *A61K 45/06* (2013.01); *C07K 7/06* (2013.01); *C07K 7/08* (2013.01); *A61K 38/00* (2013.01); *C07K 2319/00* (2013.01); *C07K 2319/09* (2013.01)

(58) Field of Classification Search
CPC ........ A61K 38/00; A61K 38/08; A61K 38/10; A61K 39/0011; A61K 39/001152; A61K 45/06; A61P 35/00; A61P 43/00; C07K 14/82; C07K 2319/00; C07K 2319/09; C07K 7/06; C07K 7/08

See application file for complete search history.

(56) References Cited

U.S. PATENT DOCUMENTS

| | | | |
|---|---|---|---|
| 9,241,920 B2* | 1/2016 | Aifantis ................. | A61K 45/06 |
| 10,370,434 B2 | 8/2019 | Soucek et al. | |
| 2007/0219271 A1 | 9/2007 | Mittman | |
| 2009/0304805 A1 | 12/2009 | Desai | |
| 2016/0058875 A1* | 3/2016 | Ryan ...................... | A61K 47/61 |
| | | | 424/133.1 |

FOREIGN PATENT DOCUMENTS

| | | |
|---|---|---|
| CN | 1968689 A | 5/2007 |
| EP | 1342781 A1 | 9/2003 |
| WO | WO1993/019176 A1 | 9/1993 |
| WO | WO-1994009133 A1 | 4/1994 |
| WO | WO2011/097522 A2 | 8/2011 |
| WO | WO2011/157713 | 12/2011 |
| WO | WO2013/063560 | 5/2013 |

OTHER PUBLICATIONS

Altscul, S., et al., "basic Local Alignment Search Tool," J. Mol. Biol. 1990;215: 403-410.
Amati, et al., (2001) Function of the c-Myc oncoprotein in chromatin remodeling and transcription. Biochim. Biophys. Acta, 1471: M135-M145.
Baudino, et al., (2001) The Max Network Gone Mad. Mol. Cell. Biol., 21; 691-702.
Beaulieu M.E. et al., "Methods for the Expression, Purification, Preparation, and Biophysical Characterization of Constructs of the c-Myc and Max b-HLH-LZs," 2013 (Methods Mol Biol, 1012:7-20).
Beaulieu M.E., et al., "New structural determinants for c-Myc specific heterodimerization with Max and development of a novel homodimeric c-Myc b-HLH-LZ," 2012 (J Mol Recognit, 25(7): 414-26).
Bidwell, G.L., et al., "Targeting a c-Myc inhibitory polypeptide to specific intracellular compartments using cell penetrating peptides:" Journal of Controlled Release, vol. 135, No. 1, 2009, pp. 2-10.
Bordo et al., "Suggestions for 'Safe' Residue Substitutions in Site-directed Mutagenesis," (J. Mol. Biol, 1991, 217; 721-739).
Brodsky, J.L. (1998) Translocation of proteins across the endoplasmic reticulum membrane. Int. rev. Cyt. 178, 277-328.
Dang et al., (1998) Identification of the human c-Myc protein nucleur translocation signal. Mol. Cell. Biol. 8(10):4048.
Delmore et al., (2011) BET bromodomain inhibition as a therapeutic strategy to target c-Myc. Cell. 146(6): 904-917.
Draeger et al., (1994) Interaction of the bHLH-zip domain of c-Myc with H1-type peptides. J. Biol. Chem. 269(3): 1785-1793.
Evan, G. (2012) Taking a back door to target Myc. Science 335, 293-294.

(Continued)

*Primary Examiner* — Marcela M Cordero Garcia
(74) *Attorney, Agent, or Firm* — Dechert LLP; Andrea L. C. Reid; Gang Wang

(57) ABSTRACT

The invention relates to a Myc dominant negative mutant, called Omomyc, for use in medicine and for use in the prevention and/or treatment of cancer. The invention also refers to a fusion protein comprising Omomyc and pharmaceutical composition thereof and their use in medicine and, in particular, for treatment of cancer.

23 Claims, 11 Drawing Sheets

Specification includes a Sequence Listing.

(56) References Cited

OTHER PUBLICATIONS

Felscher, et al., (1999) Reversible tumorigenesis by Myc in hematopoietic lineages. Mol. Cell, 4: 199-207.
Fukazawa et al., (2010) Inhibition of Muc effectively targets KRAS mutation-positive lung cancer expressing high levels of Myc. Anticancer Res. Oct; 30(10):4193-200.
Gautam et al., (2013) In silico approaches for designing highly effective cell penetrating peptides. J. Transl. Med., 11:74.
Gorlich D., "Transport into and out of the cell nucleus," (1998) EMBO 5.17:2721-7.
Grandori, et al., (2000) The Myc/Max/Mad Network and the Transcriptional Control of Cell Behavior. Annu. Rev. Cell Dev. Biol., 16:653-699.
Harahan, et al., (2011) Hallmarks of Cancer: The Next Generation. Cell 144, 646-674.
Hariton-Cazal, et al., (2002) Trageting of Nonkaryophilic Cell-Permeable Peptides into the Nuclei of Intact Cells by Covalently Attachede Nuclear Localization Signals. Biochemistry, 41(29), 9208-9214.
Kato, et al., (1992) Max: functional domains and interaction with c-Myc. Genes Dev., 6(1), 81-92.
Kyte and Doolittle, J. (1982) a simple method for displaying the hydropathic character of a protein. Mol. Biol. (1982) 157, 105-132.
Levens, D. (2010) "You Don't Much with MYC" Genes Cancer 1, 547-554.
Lindgren, et al., (2000) Cell-penetrating Peptides. Trends in pharmacological sciences, 21(3), 99-103.
Meyer, N. et al., (2008) Reflecting on 25 years with Myc. Nat Rev Cancer 8, 976-990.
Montagne, M. et al., "The Max b-HLH-LZ can transduce into cells and inhibit c-Myc transcriptional activities", PLos One, vol. 7, No. 2, 2012, pp. 1-9.
Nair et al., (2003) X-ray Structures of Myc-Max and Mad-Max Recognizing DNA: Molecular Cases of Regulation by Proto-Oncogenic Transcription Factors. Cell, vol. 112, 193-205.
Nasi, S., et al., (2001) Making decisions through Myc. FEBS Lett., 490: 153-162.
Polevoda (JBC, vol. 275, No. 47, Nov. 2000, pr. 36479-36482, of record) (Year: 2000).
Ponzielli, R. et al., "Cancer therapeutics: Targeting the dark side of Myc", European Journal of Cancer, vol. 41, No. 16, 2005, pp. 2485-2501.
Prochonik et al., (2010) Therapeutics Targeting of Myc. Genes & Cancer, vol. 1, 650-659.
Savino (The Action Mechanism of Myc Inhibitor Termed Omomyc May Give Clues on How to Target Myc for Cancer Therapy, PLoS ONE 2011, 6(7), of record) (Year: 2011).
Sodir et al., (2011) Endogenous Myc Maintains the Tumor Microenvironment. Genes and Dev., 25: 907-916.
Soucek, L. et al., "Design and properties of a Myc derivative that efficiently homodimerizes", Oncogene, vol. 17, No. 19, 1998, pp. 2463-2472.
Soucek, L. et al., "Omomyc, a potential Myc dominant negative, enhances Myc-induced apoptosis", Cancer Research, vol. 62, No. 12, 2002, pp. 3507-3510.
Soucek et al., (2004) Omomyc expression in skin prevents Myc-induced papillomatosis. Cell Death and Differentiation, 11, 1038-1045.
Soucek et al., (2008) Modelling Myc Inhibition as a Cancer Therapy. Nature, vol. 455.
Taylor et al., "The Classification of Amino Acid Conservation," (J. Theor. Biol., 1986, 119:205-218).
Terpe K., "Overview of tag protein fusions: from molecular and biochemical fundamentals to commercial systems," Appl. Microbiol. Biotechnol. 2003, 60:523-525.
Thompson et al., "CLUTAL W:improving the sensitivity of progressive multiple sequence alignment through sequence weighting, position-specific gap penalties and weight matrix choice," (1994) Nucleic Acids Res 22:4673-4680.
Trabulo et al., (2010) Cell-Penetrating Peptides—Mechanisms of Cellular Uptake and Generation of Delivery Systems. Pharmaceuticals, 3(4), 961-993.
Von Eyss et al., (2011) Addicted to Myc—but why? Genes and Dev. 25; 895-897.
Wang et al. "Construction of cell penetrating peptide vectors with N-terminal stearylated nuclear localization signal for targeted delivery of DNA into the cell nuclei." *J. Control Release*. 2011. 155(1):26-33.
Whitfield et al., (2012) Tumor Microenvironment: Becoming Sick of Myc. Cell Mol. Life Sci., 69(6), 931-934.
Wood et al., (2000) An ATPase/Helicase Complex is an Essential Cofactor for Oncogenic Transformation by c-Myc Mol. Cell. Biol., 21: 691-702.
Zuber, et al., (2011) RNAi screen identifies Brd4 as a therapeutic target in acute myeloid leukaemia. Nature 4 78, 524-528.
English Translation of Abstract for Chinese Patent Publication CN 1968689 Published May 23, 2007 (1pg.).
International Search Report issued by the International Searching Authority (ISA/O.E.P.M) dated Jul. 22, 2014 in connection with International Application No. PCT/EP2014/059315.
Ianevski et al., "SynergyFinder: a web application for analyzing drug combination dose-response matrix data," Bioinformatics. 2017; 33(15):2413-2415.
Rutledge "Cloning, Version 2", Schepartz Lab, retrieved from the Internet, 10 pages.
Soucek et al., "Inhibition of Myc family proteins eradicates KRas-driven lung cancer in mice," Genes Dev. 2013; 27(5):504-13.
Stewart et al., "Cell-penetrating peptides as delivery vehicles for biology and medicine," Org Biomol Chem. 2008; 6(13):2242-55.
Van Den Berg et al., "Protein transduction domain delivery of therapeutic macromolecules," Curr Opin Biotechnol. Dec. 2011;22(6):888-93.
Yadav et al., "Searching for drug synergy in complex dose-response landscapes using an interaction potency model," Comput Struct Biotechnol J. 2015; 13: 504-513.
Zheng et al., "ZIP: Calculate Delta Synergy Score Based on ZIP Model," Apr. 4, 2021, 3 pages. Downloaded from https://rdrr.io/bioc/synergyfinder/man/ZIP.html.

* cited by examiner

C

D

A

B

METHODS AND COMPOSITIONS FOR THE TREATMENT OF CANCER

SEQUENCE LISTING

The instant application contains a Sequence Listing which has been submitted electronically in ASCII format and is hereby incorporated by reference in its entirety. Said ASCII copy, created on Nov. 6, 2015, is named 151106_0206_88098_Substitute_Sequence_Listing_SC.txt and is 21 kilobytes in size.

FIELD OF THE INVENTION

The invention relates to the field of cancer and, more particularly, to methods and compositions for the treatment of cancer using the Omomyc polypeptide and to compositions comprising Omomyc and one or more anticancer drugs and their use for the treatment of cancer.

BACKGROUND OF THE INVENTION

The ideal cancer drug should target a non-redundant function continuously necessary for tumor maintenance, but dispensable for maintenance and function of any normal tissues. Hence, the most common logic is to target gene products that are specifically mutated in cancer, on the basis that these mutant molecules would be the likely "drivers" of the cancer and, perhaps, less critical for normal tissues. For these reasons, much attention has focused on cataloguing recurring lesions in specific cancer types. Unfortunately, there are several problems to this approach. First, most solid human cancers pass through episodes of genomic instability and exhibit a mutational noise that can obscure the "driver" mutations and their attendant effector pathways. Second, cancers are the end result of a process that involves transitions through multiple evolutionary bottlenecks. Each bottleneck may require a specific type of mutation whose function is thereafter dispensable for tumor maintenance and, consequently, not a good therapeutic target after that point in the tumor's evolution.

Myc is a basic helix-loop-helix leucine zipper (b-HLH-LZ) protein involved in growth control and cancer, which operates in a network with the structurally related proteins Max, Mad and Mnt. Myc/Max dimers activate gene transcription and induce cell proliferation or apoptosis. Mad/Max and Mnt/Max complexes act as repressors and cause cell growth arrest and differentiation. All dimers recognize the same DNA consensus site, the CACGTG E-box.

Myc is tightly regulated in normal cells, where its levels are higher in proliferating and lower in non-proliferating. Aberrantly high and/or deregulated Myc activity is causally implicated in most cancers and often associated with aggressive, poorly differentiated and angiogenic tumors. The deregulation of Myc expression is due to overexpression through gene amplifications, loss of transcriptional control, impaired degradation or increased stabilization. This results in aberrant proliferation, increased survival, changes in metabolism, angiogenesis and inflammation, all of which represent major hallmarks of cancer. Multiple studies substantiated the crucial role of Myc in governing intracellular and extracellular aspects of tumorigenesis suggesting that targeting its function would be therapeutically valuable.

It is known that down-regulation of myc by a BET bromodomain inhibitor results in the regression of multiple tumor types (Delmore, J. E., et a., 2011, Cell, 146: 904-917). While this approach displays good potential, it presents some limitations such as toxicity and numerous off targets effects.

Many small molecules disrupting the Myc/Max interaction have displayed low specificity in cellulo (Prochownik, E. V. and Vogt, P. K., 2010, Genes Cancer 1, 650-659).

A Myc inhibitor, however, has yet to become clinically available and its design presents various caveats: first, Myc is a nuclear transcription factor, which is consequently more difficult to reach than membrane or cytoplasmic molecules; second, Myc does not have an enzymatic "active site" that could be targeted; third, the Myc family comprises 3 different proteins, c-, N and L-Myc, which in certain conditions are functionally redundant, so all of them require simultaneous inhibition. Furthermore, there have been concerns that Myc inhibition would induce serious side effects by inhibiting proliferation of normal tissues. For all these reasons, making a Myc inhibitor drug is challenging.

Omomyc is a dominant-negative MYC mutant comprising the b-HLH-LZ domain of Myc and harboring four amino acid substitutions in the leucine zipper of Myc (Soucek, L. et al., 1998, Oncogene 17, 2463-2472; Soucek, L. et al. (2002), Cancer Res 62: 3507-3510). The amino acid substitutions E61T, E68I, R74Q, and R75N confer altered dimerization specificity to the protein, which retains the ability to bind its natural partner Max and to form homodimers and heterodimers with wild type c-, N- and L-Myc.

Because of these properties, Omomyc is able to prevent Myc-dependent gene transactivation functions both in vitro and in vivo by negating the ability of Myc to bind its DNA recognition binding site, the E box (Savino, M. et al., 2011, PLoS One 6, e22284; Soucek, L. et al. (2004), Cell Death Differ 11, 1038 1045). At the same time, Omomyc strongly potentiates Myc-induced apoptosis in a manner dependent on Myc expression level and thereby strengthens Myc transrepression activity. Omomyc thus prevents Myc binding to promoter E-boxes and transactivation of target genes while retaining Miz-1-dependent binding to promoters and transrepression. In the presence of Omomyc, the Myc interactome is channeled to repression and its activity switches from a pro-oncogenic to a tumor-suppressive one.

TRE-Omomyc;CMVrtTA mice, in which Omomyc expression is controlled by a tetracycline-responsive promoter element and the widely expressed rtTA transactivator is driven by a CMV promoter, exhibit high Omomyc expression in most tissues following administration of doxycycline (Soucek et al., 2008, Nature, 455: 679-683). These mice were crossed with the well-established LSL-Kras$^{G12D}$ murine model of lung tumorigenesis. Just 3 days of Omomyc expression were sufficient to cause dramatic shrinkage of the tumors and one week renders the animals essentially tumor free. Importantly, although other dividing tissues, such as skin, testis and intestine, exhibited significantly decreased proliferation rates during the treatment, and displayed a certain degree of atrophy, the mice exhibited no obvious signs of distress or disease. Moreover, the side effects of Myc inhibition resulting from Omomyc expression are completely reversible and disappear upon discontinuation of the treatment.

To date, despite the fact that the expression of Omomyc has proven to be an efficacious Myc inhibiting strategy in vivo, it has been applied solely using a gene therapy approach. Indeed, Omomyc is a peptide considered too bulky and unfit for delivery to the desired cellular compartment (Montagne M. et al., PLoS One. 2012; 7:e32172. doi: 10.1371/journal.pone.0032172), Savino M. et al., PLoS One. 2011; 6:e22284. doi: 10.1371/journal.pone.0022284) and Genes Dev., 2011, 25: 895-7. doi: 10.1101/gad.2053311.)

Moreover, Omomyc is predicted to display poor ability to cross physiological barriers because of its intrinsic physicochemical properties (e.g. hydrophobicity, as predicted using Kyte & Doolittle hydropathy plot, Kyte J., Doolittle R. F. (1982) J. Mol. Biol. 157:105-132). In addition, despite the presence of several arginine residues within the basic region of Omomyc, the most recent algorithms predicting spontaneous cell-penetration capacity of peptides do not predict Omomyc to possess such property (Gautam et al. Journal of Translational Medicine 2013, 11:74).

Therefore, providing therapeutic approaches for the treatment of cancer based on b-HLH-LZ domains capable of transducing across the cellular membrane of eukaryotic cells and inhibiting Myc-dependent gene transactivation would be advantageous.

BRIEF SUMMARY OF THE INVENTION

In a first aspect, the invention refers to a polypeptide of SEQ ID NO: 1 or a functionally equivalent variant thereof for use in medicine as well as for use in the prevention and/or treatment of cancer.

In another aspect the invention refers to a fusion protein comprising:
  (i) the polypeptide of SEQ ID NO: 1 or a functionally equivalent variant thereof and
  (ii) a cell-penetrating peptide sequence and/or a nuclear localization signal.

In another aspect, the invention refers to a pharmaceutical composition comprising the fusion protein according to the invention as well as to the use of the fusion protein in medicine and, in particular, for the treatment of cancer.

In another aspect, the invention relates to a composition comprising together or separately:
  (i) a polypeptide of SEQ ID NO: 1, a functionally equivalent variant thereof or a fusion protein according to the invention and
  (ii) an antitumoral agent.

In another aspect, the invention refers to a pharmaceutical composition comprising the composition of the invention as well as the use of the composition of the invention in medicine and, in particular, for the treatment of cancer.

DETAILED DESCRIPTION OF THE INVENTION

Figure 1:
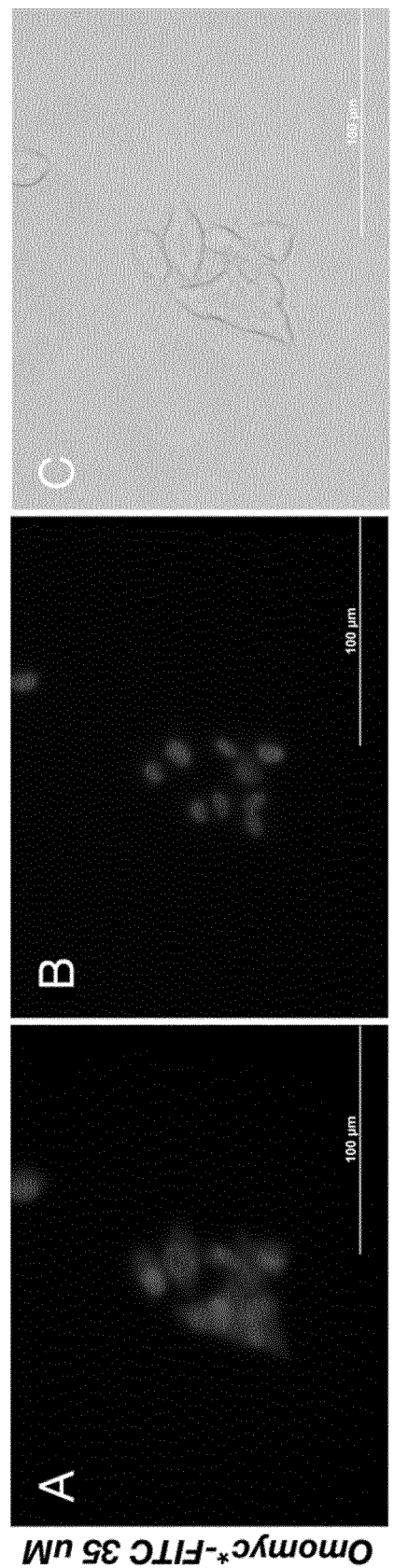
FIG. 1. (A) Fluorescence imaging of A549 cells incubated for 2 h with Omomyc-FITC at 37° C. shows that Omomyc-FITC is localized in the nucleus and cytoplasm (B) Hoescht staining of the nuclei. (C) Phase contrast.

The authors of the present invention have found that, surprisingly, Omomyc is capable of efficiently transducing across the cellular membrane and translocate to the nucleus, wherein it exerts its tumor-suppressive effect. Therefore, Omomyc is a bona fide Protein Transduction Domain (PTD). Hence, for the first time Omomyc can be used itself as an anti-Myc drug without the need of either using vehicles for delivery of the polypeptide to the cytoplasm of the cell or using gene therapy approaches for delivery the nucleic acid encoding Omomyc to the cell. This allows the use of the Omomyc polypeptide for the treatment of diseases associated with deregulated cell proliferation such as cancer. The authors of the present invention have surprisingly found that Omomyc has several advantages in comparison to the bHLHZ domain of Max (Max*):
  Omomyc shows greater cell penetrating ability in comparison to Max* in different cell types and at different concentrations (Example 6)
  Omomyc is more thermally stable than Max* and this is a clear advantage for drug design (Example 5)
  Omomyc is more efficient than Max* in both preventing the growth of cells (Example 8) and increasing death of cancer cells (Example 4).
  In addition, Omomyc is capable of crossing the blood-brain barrier (Example 9 and FIG. 10B) and exerting its therapeutic effect in vivo (Example 10).

Therapeutic Methods Using Omomyc

The present invention provides methods for the treatment of cancer based on the use of a polypeptide having the sequence of SEQ ID NO: 1, which corresponds to Omomyc, or of a functionally equivalent variant thereof.

In a first aspect, the invention refers to a polypeptide of SEQ ID NO: 1 or a functionally equivalent variant thereof for use in medicine.

In another aspect, the invention refers to a polypeptide of SEQ ID NO: 1 or a functionally equivalent variant thereof for use in the prevention and/or treatment of cancer.

In another aspect, the invention also refers to a method for the prevention and/or treatment of cancer that comprises administering to a subject in need thereof a therapeutically effective amount of the polypeptide of SEQ ID NO: 1 or a functionally equivalent variant thereof.

In another aspect, the invention also refers to the polypeptide of SEQ ID NO: 1 or a functionally equivalent variant thereof for the preparation of a medicament for the prevention and/or treatment of cancer.

The polypeptide of sequence SEQ ID NO: 1 corresponds to the Omomyc protein sequence. The term "Omomyc" as used herein, refers to a polypeptide which consists of a mutated version of the bHLHZip domain of the Myc carrying the E61T, E68I, R74Q and R75N mutations (wherein the numbering of the mutated positions is given with respect to the sequence of Myc region corresponding to amino acids 365-454 of the polypeptide as defined under accession number NP_002458 in the NCBI database, release of Jun. 27, 2012). The sequence of c-Myc provided in the NCBI database under the accession number NP_002458 is shown below, wherein the region from which Omomyc derives is shown underlined:

```
                                                       (SEQ ID NO: 2)
  1 mdffrvvenq qppatmplnv sftnrnydld ydsvqpyfyc deeenfyqqq qqselqppap 61 sediwkkfel lptpplspsr rsglcspsyv avtpfslrgd ndggggsfst adqlemvtel 121 lggdmvnqsf icdpddetfi kniiiqdcmw sgfsaaaklv seklasyqaa rkdsgspnpa 181 rghsvcstss lylqdlsaaa secidpsvvf pyplndsssp kscasqdssa fspssdslls 241 stesspqgsp eplvlheetp pttssdseee qedeeeidvv svekrqapgk rsesgspsag 301 ghskpphspl vlkrchvsth qhnyaappst rkdypaakrv kldsvrvlrq isnnrkctsp 361 rssdteenvk rrthnvlerq rrnelkrsff alrdqipele nnekapkvvi lkkatayils 421 vqaeeqklis eedllrkrre qlkhkleqlr nsca
```

The polynucleotide encoding Omomyc (SEQ ID NO: 3) and the corresponding polypeptide sequence (SEQ ID NO: 1) is shown below, wherein the underlined and bold triplets correspond to those positions which are mutated with respect to Myc:

¹ACC GAG GAG AAT GTC AAG AGG CGA ACA CAC AAC GTC
  TTG GAG CGC CAG

¹Thr Glu Glu Asn Val Lys Arg Arg Thr His Asn Val
  Leu Glu Arg Gln

⁴⁹AGG AGG AAC GAG CTA AAA CGG AGC TTT TTT GCC CTG
  CGT GAC CAG ATC

¹⁷Arg Arg Asn Glu Leu Lys Arg Ser Phe Phe Ala Leu
  Arg Asp Gln Ile

⁹⁷CCG GAG TTG GAA AAC AAT GAA AAG GCC CCC AAG GTA
  GTT ATC CTT AAA

³³Pro Glu Leu Glu Asn Asn Glu Lys Ala Pro Lys Val
  Val Ile Leu Lys

¹⁴⁵AAA GCC ACA GCA TAC ATC CTG TCC GTC CAA GCA GAG
  ACG CAA AAG CTC

⁴⁹Lys Ala Thr Ala Tyr Ile Leu Ser Val Gln Ala Glu
  Thr Gln Lys Leu

¹⁹³ATT TCT GAA ATC GAC TTG TTG CGG AAA CAA AAC GAA
  CAG TTG AAA CAC

⁶⁵Ile Ser Glu Ile Asp Leu Leu Arg Lys Gln Asn Glu
  Gln Leu Lys His

²⁴¹AAA CTT GAA CAG CTA CGG AAC TCT TGT GCG TAA

⁸¹Lys Leu Glu Gln Leu Arg Asn Ser Cys Ala End

Omomyc also contains the M2 domain of c-Myc, having the sequence RQRRNELKRSF (SEQ ID NO: 49) (see Dang and Lee, Mol. Cell. Biol., 1988, 8:4048-4054) (double underlined above), and which corresponds to a nuclear localization signal.

Omomyc is characterized in that it shows increased dimerization capacity with all three oncogenic Myc proteins (c-Myc, N-Myc and L-Myc). Omomyc can derive from the bHLHZip domain of any Myc protein known in the art, provided that the mutations which result in the tumor suppressor effect are preserved. Thus, the Omomyc that can be used in the present invention may derive from any mammal species, including but not being limited to domestic and farm animals (cows, horses, pigs, sheep, goats, dog, cats or rodents), primates and humans. Preferably, the Omomyc protein is derived from human Myc protein (accession number NP 002458, release of Jun. 27, 2012).

The term "Myc", as used, herein, refers to a family of transcription factors which includes c-Myc, N-Myc and L-Myc. Myc protein activates expression of many genes through binding on consensus sequence CACGTG (Enhancer Box sequences or E-boxes and recruiting histone acetyl-transferases or HATs). However, Myc can also act as a transcriptional repressor. By binding the Miz-1 transcription factor and displacing p300 co-activator, it inhibits expression of Miz-1 target genes. Myc also has a direct role in the control of DNA replication.

The Myc b-HLH-LZ or Myc basic region helix-loop-helix leucine zipper domain refers to a region which determines Myc dimerization with Max protein and binding to Myc-target genes. This region corresponds to amino acids 365-454 of human Myc and is characterized by two alpha helices connected by a loop (Nair, S. K., & Burley, S. K., 2003, Cell, 112: 193-205).

The term "functionally equivalent variant", when referring to Omomyc, refers to any polypeptide which results from the deletion, insertion or addition of one or more amino acids with respect to the polypeptide of SEQ ID NO:1 or which results from the chemical modification of the polypeptide of SEQ ID NO: 1 and which substantially preserves the tumor suppressor activity of the Omomyc polypeptide. The skilled person will understand that the preservation of the tumor suppressor activity of Omomyc requires that the variant can dimerize with Myc and inhibit its activity once found in the nucleus, that it is capable of translocating across the cell membrane and that it is capable of translocating across the nuclear envelope.

Suitable functionally equivalent variants of Omomyc include polypeptides consisting essentially of the polypeptide of SEQ ID NO:1. In this context, "consisting essentially of" means that the specified molecule would not contain any additional sequences that would alter the activity of Omomyc.

Suitable functional variants of the targeting peptide are those showing a degree of identity with respect to the peptide of SEQ ID NO:1 of about greater than 25% amino acid sequence identity, such as 25% 40%, 60%, 70%, 80%, 90%, 91%, 92%, 93%, 94%, 95%, 96%, 97%, 98% or 99%. The degree of identity between two polypeptides is determined using computer algorithms and methods that are widely known for the persons skilled in the art. The identity between two amino acid sequences is preferably determined by using the BLASTP algorithm as described previously [BLAST Manual, Altschul, S., et al., NCBI NLM NIH Bethesda, Md. 20894, Altschul, S., et al., J. Mol. Biol. 1990; 215: 403-410]. In a preferred embodiment, the sequence identity is determined throughout the whole length of the polypeptide of SEQ ID NO:1 or throughout the whole length of the variant or of both.

The functionally equivalent variants of the Omomyc polypeptide may also include post-translational modifications, such as glycosylation, acetylation, isoprenylation, myristoylation, proteolytic processing, etc.

Alternatively, suitable functional variants of the targeting peptide are those wherein one or more positions within the Omomyc polypeptide contain an amino acid which is a conservative substitution of the amino acid present in the Omomyc protein mentioned above. "Conservative amino acid substitutions" result from replacing one amino acid with another having similar structural and/or chemical properties. For example, the following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). Selection of such conservative amino acid substitutions is within the skill of one of ordinary skill in the art and is described, for example by Dordo et al. et al., (J. Mol. Biol, 1999, 217; 721-739) and Taylor et al., (J. Theor. Biol., 1986, 119:205-218).

It will be understood that the functionally equivalent variants of Omomyc contain mutations at positions corresponding to the mutations E61T, E68I, R74Q and R75N found in Omomyc derived from human c-Myc. The position wherein said mutations have to occur in the functionally equivalent variant can be determined by a multiple sequence alignment of different Myc sequences and identified by the alignment of those positions corresponding to positions 61, 68, 74 and 75 within the sequence of Omomyc derived from human c-Myc.

A multiple sequence alignment is an extension of pairwise alignment to incorporate more than two sequences at a time. Multiple alignment methods align all of the sequences in a given query set. A preferred multiple sequence alignment program (and its algorithm) is ClustalW, Clusal2W or ClustalW XXL (see Thompson et al. (1994) Nucleic Acids Res 22:4673-4680). Once the sequences of c-Myc from different organisms and of the variant are compared (aligned) as described herein, the skilled artisan can readily identify the positions within each of the sequence corresponding to positions and introduce within the Omomyc variant mutations corresponding to the E61T, E68I, R74Q and R75N mutations found in Omomyc derived from human c-Myc.

Suitable assays for determining whether a polypeptide can be considered as a functionally equivalent variant of Omomyc include, without limitation:

Assays which measure the capacity of the polypeptide to form dimeric complexes with Max and Myc, such as the assays based on the expression of a reporter gene as described in Soucek et al. (Oncogene, 1998, 17: 2463-2472) as well as PLA (protein Ligation assay) or Co-immunoprecipitation.

Assays which measure the capacity of the polypeptide to bind to the Myc/Max recognition site within DNA (the CACGTG site), such as the electrophoretic mobility shift assay (EMSA) described in Soucek et al. (supra.)

Assays which measure the capacity to repress Myc-induced transactivation, such as the assay based on the expression of a reporter gene under the control of the DNA binding sites specific for Myc/Max as described by Soucek et al. (supra.).

Assays based on the capacity of the polypeptide to inhibit growth of cells expressing the myc oncogene, as described by Soucek et al. (supra.).

Assays which measure the ability of the polypeptide to enhance myc-induced apoptosis, such as the assays described by Soucek et al. (Oncogene, 1998: 17, 2463-2472). Moreover, any assay commonly known in the art for assessing apoptosis in a cell can be used, such as the Hoechst staining, Propidium Iodide (PI) or Annexin V staining), trypan blue, DNA laddering/fragmentation and TUNEL.

In a preferred embodiment, a polypeptide is considered a functionally equivalent variant of Omomyc if it shows an activity in one or more of the above assays which is at least 10%, 20%, 30%, 40%, 50%, 60%, 70%, 80%, 90% or 100% of the native Omomyc.

Additionally, functionally equivalent variants of Omomyc are also capable of transducing cells after the variant is contacted with said cell. It will be understood that functionally equivalent variants of Omomyc contain the protein transducing domain found in native Omomyc or another functional protein transducing domain.

The term "cell penetrating peptide sequence" is used in the present specification interchangeably with "CPP", "protein transducing domain" or "PTD". It refers to a peptide chain of variable length that directs the transport of a protein inside a cell. The delivering process into cell commonly occurs by endocytosis but the peptide can also be internalized into cell by means of direct membrane translocation. CPPs typically have an amino acid composition that either contains a high relative abundance of positively charged amino acids such as lysine or arginine or has sequences that contain an alternating pattern of polar/charged amino acid and non-polar, hydrophobic amino acids. Examples of CPPs which can be used in the present invention include, without limitation, the CPP found in *Drosophila antennapedia* protein (RQIKIWFQNRRMKWKK. SEQ ID NO:4), the CPP found in the herpesvirus simplex 1 (HSV-1) VP22 DNA-binding protein (DAATATRGRSAASRPTERPRAPAR-SASRPRRPVE, SEQ ID NO:5), the CPP of Bac-7 (RRIR-PRPPRLPRPRPRPLPFPRPG; SEQ ID NO: 6), the CPPs of the HIV-1 TAT protein consisting of amino acids 49-57 (RKKRRQRRR, SEQ ID NO: 7), amino acids 48-60 (GRKKRRQRRRTPQ, SEQ ID NO: 8), amino acids 47-57 (YGRKKRRQRRR; SEQ ID NO: 9); the CPP of 5413-PV peptide (ALWKTLLKKVLKAPKKKRKV; SEQ ID NO: 10), the CPP of penetratin (RQIKWFQNRRMKWKK; SEQ ID NO: 11), the CPP of SynB1 (RGGRLSYSRRRFST-STGR; SEQ ID NO: 12), the CPP of SynB3 (RRLSYS-RRRF; SEQ ID NO:13), the CPP of PTD-4 (PIRRRKKLRRLK; SEQ ID NO: 14), the CPP of PTD-5 (RRQRRTSKLMKR; SEQ ID NO: 15), the CPP of the FHV Coat-(35-49) (RRRRNRTRRNRRRVR; SEQ ID NO: 16), the CPP of BMV Gag-(7-25) (KMTRAQR-RAAARRNRWTAR; SEQ ID NO: 17), the CPP of HTLV-II Rex-(4-16) (TRRQRTRRARRNR; SEQ ID NO:18), the CPP of D-Tat (GRKKRRQRRRPPQ; SEQ ID NO:19), the CPP R9-Tat (GRRRRRRRRRPPQ; SEQ ID NO: 20), the CPP of MAP (KLALKLALKLALALKLA; SEQ ID NO: 21), the CPP of SBP (MGLGLHLLV-LAAALQGAWSQPKKKRKV; SEQ ID NO: 22), the CPP of FBP (GALFLGWLGAAGSTMGAWSQPKKKRKV; SEQ ID NO: 23), the CPP of MPG (ac-GALFLGFL-GAAGSTMGAWSQPKKKRKV-cya; SEQ ID NO: 24), the CPP of MPG(ENLS) (ac-GALFLGFL-GAAGSTMGAWSQPKSKRKV-cya; SEQ ID NO: 25), the CPP of Pep-1 (ac-KETWWETWWTEWSQPKKKRKV-cya; SEQ ID NO: 26), the CPP of Pep-2 (ac-KETWFETWFTEWSQPKKKRKV-cya; SEQ ID NO: 27), a polyarginine sequence having the structure RN (wherein N is between 4 and 17), the GRKKRRQRRR sequence (SEQ ID NO: 28), the RRRRRRLR sequence (SEQ ID NO: 29), the RRQRRTS KLMKR sequence (SEQ ID NO: 30); Transportan GWTLNSAGYLLGKINLKALAALAKKIL (SEQ ID NO: 31); KALAWEAKLAKALAKALAKHLAKA-LAKALKCEA (SEQ ID NO: 32); RQIKIWFQNRRMKWKK (SEQ ID NO: 33), the YGRKKRRQRRR sequence (SEQ ID NO: 34); the RKKRRQRR sequence (SEQ ID NO: 35); the YARAAAR-QARA sequence (SEQ ID NO: 36); the THRLPRRRRRR sequence (SEQ ID NO: 37); the GGRRARRRRRR sequence (SEQ ID NO: 38).

Suitable assays for determining whether a polypeptide preserves the cell membrane translocation capacity of Omomyc include, without limitation, assays which measure the capacity of the polypeptide to transduce cells in culture, such as the assay shown in example 3 of the present invention. This assay is based on contacting the polypeptide with culture cells and detecting the presence of the polypeptide in an intracellular location. In a preferred embodiment, the detection of the polypeptide of the invention is performed by fluorescence microscopy.

In a preferred embodiment, a polypeptide is considered as a functionally equivalent variant of Omomyc if it is capable of transducing a target cell at least 10%, 20%, 30%, 40%, 50%, 60%, 70%, 80%, 90% or 100% as efficiently as native Omomyc.

Additionally, functionally equivalent variants of Omomyc are also capable of reaching the nuclei of the transduced cells after the variant is contacted with said cell. It will be understood that functionally equivalent variants of Omomyc contain the NLS found in native Omomyc or another functional NLS.

The term "nuclear localization signal", as used herein, refers to an amino acid sequence of about 4-20 amino acid residues in length, which serves to direct a protein to the nucleus. Typically, the nuclear localization sequence is rich in basic amino acids and exemplary sequences are well known in the art (Gorlich D. (1998) EMBO 5.17:2721-7). In some embodiments, the NLS is selected from the group consisting of the SV40 large T Antigen NLS (PKKKRKV, SEQ ID NO: 39); the Nucleoplasmin NLS (KRPAATKK-AGQ AKKKK, SEQ ID NO: 40); the CBP80 NLS (RRRHS-DENDGGQPHKRRK, SEQ ID NO: 41); the HIV-I Rev protein NLS (RQARRNRRRWE, SEQ ID NO: 42); the HTLV-I Rex (MPKTRRRPRRSQRKRPPT, SEQ ID NO: 43); the hnRNP A NLS (NQSSNFGPMKGGNFG-GRSSGPYGGGGQYFKPRNQGGY, SEQ ID NO: 44); the rpL23a NLS (VHSHKKKKIRT-SPTFTTPKTLRLRRQPKYPRKSAPRRNKLDHY, SEQ ID NO: 45). In one embodiment of the invention, the nuclear localization signal comprises the motif K (K/R)×(K/R) (SEQ ID NO: 46).

Suitable assays for determining whether a polypeptide is a functionally equivalent variant of Omomyc in terms of its ability to translocate across the cellular membrane include double labelling of a cell with a reagent specific for the polypeptide and with a dye which specifically labels the nucleus of the cell (such as DAPI or Hoechst dye). Such assays are shown in Example 6 of the present invention. In a preferred embodiment, the detection of the polypeptide of the invention is performed by confocal microscopy or by fluorescence microscopy.

In a preferred embodiment, a polypeptide is considered as a functionally equivalent variant of Omomyc if it is capable of translocating to the nucleus of the target tumor cells at least 10%, 20%, 30%, 40%, 50%, 60%, 70%, 80%, 90% or 100% as efficiently as native Omomyc.

Suitable functionally equivalent variants include the polypeptides Omomyc*TAT and Omomyc*LZArg as defined below:

| Name | SEQ ID NO: | Sequence |
|---|---|---|
| Omomyc*TAT | 47 | MTEENVKRRTHNVLERQRRNELKRSF-FALRDQIP ELENNEKAPKVVILKKATAYILSVQAETQK-LISE IDLLRKQNEQLKHKLEQLRNSCAGRKKRRQRRR |
| Omomyc*LZArg | 48 | MTEENVKRRTHNVLERQRRNELKRSF-FALRDQIP ELENNEKAPKVVILKKATAYILSVQAETQK-LISE IDLLRKQNEQLKHKLEQLRNSCARRRRRRLR |

According to the invention, the Omomyc polypeptide or the functionally equivalent variant thereof are used in a method for the prevention or treatment of cancer in a subject. It will be understood that the preventive or therapeutic method according to the invention involves the direct use of the Omomyc polypeptide or of the functionally equivalent variant thereof. Thus, the preventive or therapeutic methods according to the invention do not involve the administration of the nucleic acid encoding Omomyc or the functionally equivalent variant thereof.

"Prevention" is understood as the administration of a polypeptide of SEQ ID NO: 1 or a functionally equivalent variant thereof according to the first aspect of the invention, or of a medicament containing it in an initial or early stage of the disease, or to also prevent its onset.

The term "treatment" is used to designate the administration of a polypeptide of SEQ ID NO: 1 or a functionally equivalent variant thereof according to the first aspect of the invention, or of a medicament containing it to control the progression of the disease before or after the clinical signs have appeared. Control of the progression of the disease is understood as the beneficial or desired clinical results which include but are not limited to reduction of the symptoms, reduction of the duration of the disease, stabilization of pathological conditions (specifically avoiding additional impairment), delaying the progression of the disease, improving the pathological condition and remission (both partial and complete). The control of the progression of the disease also involves a prolongation of survival in comparison to the expected survival if the treatment was not applied.

The term "cancer" is referred to a disease characterized by uncontrolled cell division (or by an increase of survival or apoptosis resistance), by the ability of said cells to invade other neighbouring tissues (invasion) or by the spread to other areas of the body where the cells are not normally located (metastasis) through the lymphatic and blood vessels. Depending on whether or not tumours can spread by invasion and metastasis, they are classified as being either benign or malignant: benign tumours are tumours that cannot spread by invasion or metastasis, i.e., they only grow locally; whereas malignant tumours are tumours that are capable of spreading by invasion and metastasis. The methods according to the present invention are useful for the treatment of local and malignant tumours. As used herein, the term cancer includes, but is not limited to, the following types of cancer: breast cancer; biliary tract cancer; bladder cancer; brain cancer including glioblastomas and medulloblastomas; cervical cancer; choriocarcinoma; colon cancer; endometrial cancer; esophageal cancer; gastric cancer; hematological neoplasms including acute lymphocytic and myelogenous leukemia; T-cell acute lymphoblastic leukemia/lymphoma; hairy cell leukemia; chronic myelogenous leukemia, multiple myeloma; AIDS-associated leukemias and adult T-cell leukemia/lymphoma; intraepithelial neoplasms including Bowen's disease and Paget's disease; liver cancer; lung cancer; lymphomas including Hodglun's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; slun cancer including melanoma, Merkel cell carcinoma, Kaposi's sarcoma, basal cell carcinoma, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; and renal cancer including adenocarcinoma and Wilms tumor. Other cancers will-be known to one of ordinary skill in the art. In a preferred embodiment, the cancer treated is lung cancer, preferably lung adenocarcinoma, more preferably a KRas-driven lung adenocarcinoma.

The authors of the present invention have also observed that Omomyc or the functionally equivalent variant thereof is capable of decreasing cell proliferation irrespective of whether the cancer shows increased expression or activity of the Myc protein.

A "subject," as used herein, includes any animal that has a cancer or exhibits a symptom or cancer, or is at risk for having a cancer or exhibiting a symptom of cancer. Suitable subjects (patients) include laboratory animals (such as mouse, rat, rabbit, or guinea pig), farm animals, and domestic animals or pets (such as a cat or dog). Non-human primates and, preferably, human patients, are included.

The appropriate dosage of Omomyc or of the functionally equivalent variant thereof to be used in the methods according to the invention will depend on different factors such as the type of cancer to be treated, the severity and course of the disease, whether the composition is administered for preventive or therapeutic purposes, previous therapy, the patient's clinical history and response to the peptide or polypeptide, and the discretion of the attending physician.

The amount of polypeptide of SEQ ID NO:1, of the functionally equivalent variant thereof is suitably administered to the patient at one time or over a series of treatments. Depending on the type and severity of the disease, an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

The polypeptide of SEQ ID NO:1, or of the functionally equivalent variant thereof may be administered by any type of suitable route, such as by oral route, topical route, by inhalation or parenteral route so that the pharmaceutically acceptable excipients necessary for the formulation of the desired dosage form will be included. The preferred route of administration of said pharmaceutical compositions is the endovenous route. In another embodiment, the route of administration is the intranasal route.

In one embodiment, the Omomyc or the functionally equivalent variant thereof is prepared with carriers which will protect said polypeptide from a rapid elimination from the body, such as a controlled release formulation, including implants and microencapsulated administration systems. Biodegradable biocompatible polymers such as ethylene vinylacetate, polyanhydrides, polyglycolic acid, collagen, polyorthoesters and polylactic acid can be used. The processes for preparing said formulations will be clear for persons skilled in the art. The materials can also be commercially obtained in Alza Corporation and Nova Pharmaceuticals, Inc.

Despite the fact that Omomyc and functionally equivalent variants thereof are capable of translocating across biological membranes, it is possible to formulate Omomyc or any of its functionally equivalent variants in nanoparticles. The nanoparticles may contribute to preserve the integrity of the polypeptide in the biological fluids until it reaches the target organ. In addition, nanoparticles can also be modified so as to include moieties which allow the targeting of the nanoparticule to an organ of interest. In this way, Omomyc or the functionally equivalent variant thereof will be delivered in the proximity of the target organ, facilitating access of Omomyc to the interior of the cells where its biological activity is required.

Thus, in another embodiment, Omomyc or any of its functionally equivalent variants are provided forming part of a nanoparticle.

As used herein, the term "nanoparticle" refers to any material having dimensions in the 1-1,000 nm range. In some embodiments, nanoparticles have dimensions in the 2-200 nm range, preferably in the 2-150 nm range, and even more preferably in the 2-100 nm range. Nanoparticles that can be used in the present invention include such nanoscale materials as a lipid-based nanoparticle, a superparamagnetic nanoparticle, a nanoshell, a semiconductor nanocrystal, a quantum dot, a polymer-based nanoparticle, a silicon-based nanoparticle, a silica-based nanoparticle, a metal-based nanoparticle, a fullerene and a nanotube.

Targeted delivery can be achieved by the addition of ligands without compromising the ability of nanoparticles to deliver their polypeptide payloads. It is contemplated that this will enable delivery to specific cells, tissues and organs. The targeting specificity of the ligand-based delivery systems are based on the distribution of the ligand receptors on different cell types. The targeting ligand may either be non-covalently or covalently associated with a nanoparticle, and can be conjugated to the nanoparticles by a variety of methods as discussed herein.

Examples of proteins or peptides that can be used to target nanoparticles include transferin, lactoferrin, TGF-β, nerve growth factor, albumin, HIV Tat peptide, RGD peptide, and insulin, as well as others.

It will be understood that the formulation of Omomyc or of the functionally equivalent variant thereof in a nanoparticle is not intended or is not solely intended for facilitating the access of the Omomyc to the interior of the cell but to protect Omomyc from degradation and/or for facilitating targeting of the nanoparticle to the organ of interest.

Omomyc Conjugates and Fusion Proteins Comprising Omomyc

The present invention also provides conjugates which includes a first region comprising the polypeptide of SEQ ID NO:1 or a functionally equivalent variant thereof and a second region comprising a chemical moiety that facilitates cellular uptake of the polypeptide. Examples of moieties for enhancing cellular uptake include but are not limited to: a hydrophobic group (e.g., a lipid or fatty acid), a protein transducing domain, and certain metal chelates.

The presence of additional chemical moieties in the Omomyc molecule results in conjugates showing increased capability for being translocated across biological membranes with respect to unmodified Omomyc, thereby resulting in increased tumor suppressor activity.

Thus, in another aspect, the invention relates to a conjugate comprising:
(i) the polypeptide of SEQ ID NO: 1 or a functionally equivalent variant thereof, and
(ii) a chemical moiety that facilitates cellular uptake of the polypeptide.

The term "conjugate", as used herein, refers to two or more compounds which are covalently linked together so that the function of each compound is retained in the conjugate.

In preferred embodiments, the conjugates according to the invention comprise at least 1, at least 2, at least 3, at least 4, at least 5, at least 6, at least 7, at least 8, at least 9, at least 10 or more chemical moieties that facilitate cellular uptake of the polypeptide or of the functionally equivalent variant thereof.

In one embodiment, the chemical moiety that facilitates cellular uptake of the polypeptide is a lipid or a fatty acid.

A fatty acid generally is a molecule comprising a carbon chain with an acidic moiety (e.g., carboxylic acid) at an end of the chain. The carbon chain may of a fatty acid may be of any length, it is preferred that the length of the carbon chain be of at least 2, 3, 4, 5, 6, 7, 8, 9, 10, 11, 12, 13, 14, 15, 16, 17, 18, 19, 20 or more carbon atoms, and any range derivable therein. In certain embodiments, the length of the carbon chain is from 4 to 18 carbon atoms in the chain portion of the fatty acid. In certain embodiments the fatty acid carbon chain may comprise an odd number of carbon atoms, however, an even number of carbon atoms in the chain may be preferred in certain embodiments. A fatty acid comprising only single bonds in its carbon chain is called saturated, while a fatty acid comprising at least one double bond in its chain is called unsaturated. The fatty acid may be branched, though in preferable embodiments of the present invention, it is unbranched. Specific fatty acids include, but are not limited to, linoleic acid, oleic acid, palmitic acid, linolenic acid, stearic acid, lauric acid, myristic acid, arachidic acid, palmitoleic acid, arachidonic acid.

In a preferred embodiment, the chemical moiety that facilitates cellular uptake of the polypeptide is a cell penetrating peptide sequence, in which case, the conjugate is a fusion protein comprising Omomyc or the functionally equivalent variant thereof and the cell penetrating peptide sequence.

The term "fusion protein" relates to proteins generated by gene technology which consist of two or more functional domains derived from different proteins. A fusion protein may be obtained by conventional means, e.g., by means of gene expression of the nucleotide sequence encoding for said fusion protein in a suitable cell. It will be understood that the cell penetrating peptide refers to a cell penetrating peptide which is different from the cell penetrating peptide which forms part of the polypeptide of SEQ ID NO: 1 or of the a functionally equivalent variant thereof.

The terms "polypeptide of SEQ ID NO:1", "functionally equivalent variant of the polypeptide of SEQ ID NO:1" and "cell penetrating peptide" have been described in detail in the context of the medical uses of the invention and are equally applicable in the context of the fusion protein.

In a preferred embodiment, said cell-penetrating peptide is not the endogenous Omomyc cell penetrating peptide.

In one embodiment, the cell-penetrating peptide sequence is fused at the N-terminus of the polypeptide of SEQ ID NO: 1 or of the functionally equivalent variant thereof. In another embodiment, the cell-penetrating peptide is fused at the C-terminus of the polypeptide of SEQ ID NO: 1 or of the functionally equivalent variant thereof.

In preferred embodiments, the fusion proteins according to the invention comprise, in addition to the own cell penetrating peptide found in the polypeptide of SEQ ID NO:1 or of the functionally equivalent variant thereof, at least 1, at least 2, at least 3, at least 4, at least 5, at least 6, at least 7, at least 8, at least 9, at least 10 or more additional cell penetrating peptides.

In another preferred embodiment, the conjugates or fusion proteins of the invention comprise the polypeptide of SEQ ID NO: 1 or a functionally equivalent variant thereof and further comprise an N-terminal or C-terminal nuclear localization signal. The term "nuclear localization signal (NLS)" has been described in the context of the therapeutic uses of the invention and is equally applicable to the fusion proteins of the invention. It will be appreciated that the additional NLS refers to an NLS which is different to the endogenous NLS found in Omomyc or in the functionally equivalent variant thereof. The additional NLS may be the same or different to the endogenous NLS found in Omomyc or in the functionally equivalent variant thereof.

In one embodiment, the NLS is one of the NLS which appears endogenously in the Myc sequence, such as the M1 peptide (PAAKRVKLD, SEQ ID NO: 50) or the M2 peptide (RQRRNELKRSF, SEQ ID NO: 49) (see Dang and Lee, supra.).

In preferred embodiments, the conjugates or fusion proteins according to the invention comprise, in addition to the endogenous NLS found in the polypeptide of SEQ ID NO:1 or in the functionally equivalent variant thereof, at least 1, at least 2, at least 3, at least 4, at least 5, at least 6, at least 7, at least 8, at least 9, at least 10 or NLS.

The skilled person will understand that it may be desirable that the fusion protein further comprises one or more flexible peptides that connect the polypeptide of SEQ ID NO:1 or the functionally equivalent variant thereof, the cell penetrating peptide sequence and/or the NLS. Thus, in a particular embodiment the polypeptide of the invention is directly connected to the cell penetrating peptide sequence. In another particular embodiment, the polypeptide of the invention is connected to the cell penetrating peptide sequence through a flexible peptide. In a particular embodiment the polypeptide of the invention is directly connected to the cell penetrating peptide sequence and to the NLS. In another particular embodiment, the polypeptide of the invention is connected to the cell penetrating peptide sequence through a first flexible peptide linker and to the NLS through a second flexible peptide linker.

As used herein, the term "flexible peptide", "spacer peptide" or "linker peptide" refers to a peptide that covalently binds two proteins or moieties but which is not part of either polypeptide, allowing movement of one with respect to the other, without causing a substantial detrimental effect on the function of either the protein or the moiety. Thus, the flexible linker does not affect the tumour suppressor activity of the Omomyc sequence, the cell penetrating activity of the cell penetrating peptide or the nuclear localization capacity of the NLS.

The flexible peptide comprises at least one amino acid, at least two amino acids, at least three amino acids, at least four amino acids, at least five amino acids, at least six amino acids, at least seven amino acids, at least eight amino acids, at least nine amino acids, the least 10 amino acids, at least 12 amino acids, at least 14 amino acids, at least 16 amino acids, at least 18 amino acids, at least 20 amino acids, at least 25 amino acids, at least 30 amino acids, at least 35 amino acids, at least 40 amino acids, the least 45 amino acids, at least 50 amino acids, at least 60 amino acids, at least 70 amino acids, at least 80 amino acids, at least 90 amino acids, or about 100 amino acids. In some embodiments the flexible peptide will permit the movement of one protein with respect to the other in order to increase solubility of the protein and/or to improve its activity. Suitable linker regions include a poly-glycine region, the GPRRRR sequence (SEQ ID NO: 51) of combinations of glycine, proline and alanine residues.

In some embodiments the fusion protein of the invention can comprise an additional chemical moiety including, among others, fluorescence groups, biotin, polyethylene glycol (PEG), amino acid analogs, unnatural amino acids, phosphate groups, glycosyl groups, radioisotope labels, and pharmaceutical molecules. In other embodiments, the heterologous polypeptide can comprise one or more chemically reactive groups including, among others, ketone, aldehyde, Cys residues and Lys residues.

In a particular embodiment, the conjugates or fusion proteins of the invention comprise a tag bound to the conjugate or to the C-terminal or N-terminal domain of said fusion protein or variant thereof. Said tag is generally a peptide or amino acid sequence which can be used in the isolation or purification of said fusion protein. Thus, said tag is capable of binding to one or more ligands, for example, one or more ligands of an affinity matrix such as a chromatography support or bead with high affinity. An example of said tag is a histidine tag (His-tag or HT), such as a tag comprising 6 residues of histidine (His6 or H6), which can bind to a column of nickel (Ni2+) or cobalt (Co2+) with high affinity. His-tag has the desirable feature that it can bind its ligands under conditions that are denaturing to most proteins and disruptive to most protein-protein interactions. Thus, it can be used to remove the bait protein tagged with H6 following the disruption of protein-protein interactions with which the bait has participated.

Additional illustrative, non-limitative, examples of tags useful for isolating or purifying a fusion protein include Arg-tag, FLAG-tag (DYKDDDDK; SEQ ID NO:52), Strep-tag (WSHPQFEK, SEQ ID NO:53), an epitope capable of being recognized by an antibody, such as c-myc-tag (recognized by an anti-c-myc antibody), HA tag (YPYDVPDYA, SEQ ID NO:54), V5 tag (GKPIPN-PLLGLDST, SEQ ID NO:55), SBP-tag, S-tag, calmodulin binding peptide, cellulose binding domain, chitin binding domain, glutathione S-transferase-tag, maltose binding protein, NusA, TrxA, DsbA, Avi-tag, etc. (Terpe K., Appl. Microbiol. Biotechnol. 2003, 60:523-525), an amino acid sequence such as AHGHRP (SEQ ID NO:56) or PIHDHDHPHLVIHSGMTCXXC (SEQ ID NO:57), (3-galactosidase and the like.

The tag can be used, if desired, for the isolation or purification of said fusion protein.

In another aspect, the invention relates to the conjugate or fusion protein according to the invention for use in medicine.

In another aspect, the invention relates to the conjugate or fusion protein according to the invention for use in the prevention and/or treatment of cancer.

In another aspect, the invention relates to the use of the conjugate or the fusion protein according to the invention for the preparation of a medicament for the prevention and/or treatment of cancer.

In another aspect, the invention relates to a method of treatment and/or prevention of cancer in a subject which comprises the administration to said subject of the conjugate or of the fusion protein according to the invention.

In a preferred embodiment the cancer to be prevented or treated is Myc-induced cancer. In another preferred embodiment, the cancer to be prevented or treated is a cancer associated with a mutation in the KRAS gene. In one embodiment, the mutation in the KRAS gene is a mutation at the glycine at position 12, at the glycine at position 13 or at the glutamine at position 61. In a more preferred embodiment, the mutation is selected from the group consisting of the G12S mutation, the G12V mutation, the G13D mutation, the G12C mutation, the G12R mutation, the G12F mutation, the G12I mutation, the G13C mutation, the G13R mutation, or the Q61L mutation.

The terms "medicament", "prevention", "treatment", "cancer" and "Myc-induced cancer" have been defined previously and equally apply to this aspect of the invention.

Antitumor Compositions

The unexpected finding that the Omomyc polypeptide is capable of translocating across biological membranes and exerting its tumor suppressor activity when provided as a polypeptide opens the possibility of formulating Omomyc with other antitumor drugs. Thus, in another aspect, the present invention also provides compositions containing, together or separately, a first component selected from the group consisting of:

(i) Omomyc,
(ii) a functionally equivalent variant thereof,
(iii) a conjugate or fusion protein according to the invention and, as a second component, an antitumor compound.

The first component of the compositions according to the invention includes a polypeptide according to SEQ ID NO:1, a functionally equivalent variant thereof or a fusion protein according to the invention. Suitable polypeptides, functionally equivalent variants of the polypeptide of SEQ ID NO:1 and fusion proteins have been described above in the context of the therapeutic methods according to the invention and are equally applicable to the compositions according to the invention.

As used herein, "antitumoral agent" is understood as said biological or chemical compound which treat tumors or prevent the formation thereof. In a preferred embodiment said antitumoral agent is selected from the group consisting of a cytotoxic agent, an antiangiogenic agent, an antimetastatic agent and an antiproliferative agent.

As used in the present invention, the term "cytotoxic agent" relates to an agent which is capable of promoting cell death and which has capacity for reducing the growth, stopping the growth or destroying cells and, particularly, rapidly proliferating cells and, yet more particularly, tumor cells. Cell death can be caused by any mechanism, such as for example apoptosis, although it is not limited to this cause, by the metabolism inhibition, the interference with the organization of the cytoskeleton or the chemical modification of the DNA. The term cytotoxic agent comprises any chemotherapy agent including small organic molecules, peptides, oligonucleotides and the like; toxins; enzymes; cytokines; radioisotopes or radiotherapy agents.

"Chemotherapy agents" are understood as chemical compounds such as, without limitation, anthracycline antibiotics such as doxorubicin and daunorubicin, taxanes such as Taxol™ and docetaxel, vinca alkaloids such as vincristine and vinblastine, 5-fluorouracil (5-FU), leucovorin, irinotecan, idarubicin, mitomycin C, oxaliplatin, raltitrexed, tamoxifen, cisplatin, carboplatin, methotrexate, actinomycin D, mitoxantrone, blenoxane or mithramycin.

"Toxin" is understood as a toxic agent which conjugates with the polypeptide according to the first aspect of the invention or the fusion protein according to the second aspect of the invention forming an immunotoxin. The conjugation of determined toxins with said polypeptide or with said fusion protein reduces the toxicity of the former, enabling their use as therapeutic agents, because otherwise they would be too toxic. The binding between the toxin and the polypeptide according to the first aspect of the invention or the fusion protein according to the second aspect of the invention is performed chemically, conserving its biological activity. Their separation generally occurs in the lysosomes of the target cells such that the mentioned chemical binding is only broken in the enclosed acidic cellular environment provided by the lysosomes. Toxins useful in the context of the present invention are plant toxins, bacterial toxins, toxins of fungal or animal origin and fragments thereof, such as, without limitation, the ricin A-chain, saponin, the diphtheria A-chain, active non-binding fragments of the diphtheria toxin, Pseudomonas aeruginosa exotoxin A-chain, abrin A-chain, modecin A-chain, α-sarcin, Leurites fordii A-proteins, dianthin proteins, Phytolaca americana (PAPI, PAPII and PAP-S) proteins, Momordica charantia inhibitor, curcine, crotin, Saponaria officinalis inhibitor, gelonin, mitogelin, restrictocin, phenomycin, enomycin and trichothecenes.

"Enzymes" are understood in the context of the present invention as toxin or drug activating enzymes, such as, without limitation, alkaline phosphatase which activates etoposide and doxorubicin; carboxypeptidase G2 which activates nitrogen mustards; beta-lactamase which activates doxorubicin, paclitaxel and mitomycin.

"Cytokines" are understood as peptides of different sizes and molecular weights which synthesize the cells of the immune system for the purpose of regulating the immune response, and they can be hormones, growth factors, necrosis factors, etc. They can be of natural origin or from recombinant cell cultures and biologically active equivalents of natural sequence cytokines. Their conjugation with antibodies gives rise to immunocytokines. Cytokines useful in the present invention are, without limitation, TNF factor alpha, INF-gamma, GM-GSF factor or IL-2.

"Radioisotopes" is understood as radioactive isotopes such as, without limitation, $^{131}$I, $^{90}$Y, $^{177}$Lu, $^{188}$Re, $^{67}$Cu, $^{211}$At, $^{213}$Bi, $^{125}$I, $^{111}$In.

Antiangiogenic agent" is understood as a chemical or biological substance which inhibits or reduces the formation of new blood vessels, i.e., angiogenesis.

Antiangiogenic agents that can be conjugated with the polypeptide according to the first aspect of the invention or with the fusion protein according to the second aspect of the invention include, without limitation, an antiangiogenic agent selected from the group of paclitaxel, 2-methoxyestradiol, prinomastat, batimastat, BAY 12-9566, carboxyamidotriazole. CC-1088, dextromethorphan acetic acid, dimethylxanthenone acetic acid, endostatin, IM-862, marimastat, penicillamine, PTK787/ZK 222584, RPI.4610, squalamine lactate, SU5416, thalidomide, combretastatin, tamoxifen, COL-3, neovastat, BMS-275291. SU6668, anti-VEGF antibodies, Medi-522 (Vitaxin II), CAI, interleukin 12, IM862, amiloride, angiostatin, K1-3 angiostatin, K1-5 angiostatin, Captopril, DL-alpha-difluoromethylomithine, DL-alpha-difluoromethylomithine HCl, endostatin, fumagillin, herbimycin A. 4-Hydroxyphenylretinamide, juglone, laminin, laminin hexapeptide, laminin pentapeptide, lavendustin A, medroxyprogesterone, minocycline, placenta ribonuclease inhibitor, suramin, thrombospondin, antibodies directed against proangiogenic factors (for example, Avastin, Erbitux, Vectibix, Herceptin); low molecular weight tyrosine kinase inhibitors of proangiogenic growth factors (for example Tarceva, Nexavar, Sutent, Iressa); mTOR inhibitors (for example Torisel); interferon alpha, beta and gamma, IL-12, matrix metalloproteinase inhibitors (for example, COL3, marimastat, batimastat); ZD6474, SUI1248, vitaxin; PDGFR inhibitors (for example Gleevec); NM3 and 2-ME2; cyclopeptides such as cilengitide.

"Antimetastatic agent" is understood as a chemical or biological substance which inhibits or reduces metastasis, i.e., the distance propagation, fundamentally by the lymphatic or blood stream, of the cancer causing cells, and the growth of new tumors in the destination sites of said metastasis.

"Antiproliferative agent" is understood as a chemical or biological substance which is capable of preventing or inhibiting the formation or growth of tumors. Antiproliferative agents include but are not limited to (i) antimetabolites such as folic acid antimetabolites (aminopterin, denopterin, methotrexate, edatrexate, trimetrexate, nolatrexed, lometrexol, pemetrexed, raltitrexed, piritrexim, pteropterin, leucovorin, 10-propargyl-5,8-dideazafolate (PDDF, CB3717)), purine analogs (cladribine, clofarabine, fludarabine, mercaptopurine, pentostatin, thioguanine) and pyrimidine analogs (capecitabine, cytarabine or ara-C, decitabine, fluorouracil, 5-fluorouracil, doxifluridine, floxuridine and gemcitabine) (ii) natural products, such as antitumor antibiotics and mitotic inhibitors such vinca alkaloids such as vindesine, vincristine, vinblastine, vinorelbine; taxanes such as paclitaxel (Taxol™), docetaxel (Taxotere™); colchicine (NSC 757), thiocolchicine (NSC 361792), colchicine derivatives (e. g., NSC 33410), and allocolchicine (NSC 406042); halichondrin B (NSC 609395); dolastatin 10 (NSC 376128); maytansine (NSC 153858); rhizoxin (NSC 332598); epothilone A, epothilone B; discodermolide; estramustine; nocodazole; (iii) hormones and antagonist thereof, such tamoxifen, toremifene, anastrozole, arzoxifene, lasofoxifene, raloxifene, nafoxidine, fulvestrant, aminoglutethimide, testolactone, atamestane, exemestane, fadrozole, formestane, letrozole, goserelin, leuprorelin or leuprolide, buserelin, histrelin, megestrol and fluoxymesterone; (iv) biological agents, such as viral vectors, interferon alpha and interleukines; (v) platinum based compounds such as carboplatin, cisplatin [cis-diamminedichloroplatinum, (CDDP)], oxaliplatin, iproplatin, nedaplatin, triplatin tetranitrate, tetraplatin, satraplatin (JM216), JM118 [cis ammine dichloro (II)], JM149 [cis ammine dichloro (cyclohexylamine) trans dihydroxo platinum (IV)], JM335 [trans ammine dichloro dihydroxo platinum (IV)], transplatin, ZD0473, cis, trans, cis-Pt(NH3)(C6H11NH2)(OOCC3H7) 2Cl, malanate-1,2-diaminociclohexanoplatin(II), 5-sulphosalycilate-trans-(1,2-diaminociclohexane)platin (II) (SSP), poly-[(trans-1,2-diaminocyclohexane)platin]-carboxyamilose (POLY-PLAT) and 4-hydroxy-sulphonylphenylacetate (trans-1,2-diaminocyclohexane) platinum (II) (SAP) and the like and (vi) DNA-alkylating drugs such as nitrogen mustards, nitrosoureas, ethylenimine derivatives, alkyl sulfonates and triazenes, including, but not limited to, cyclophosphamide (Cytoxan™), busulfan, improsulfan, piposulfan, pipobroman, melphalan (L-sarcolysin), chlorambucil, mechlorethamine or mustine, uramustine or uracil mustard, novembichin, phenesterine, trofosfamide, ifosfamide, carmustine (BCNU), lomustine (CCNU), chlorozotocin, fotemustine, nimustine, ranimnustine, semustine (methyl-CCNU), streptozocin, thiotepa, triethylenemelamine, triethylenethiophosphoramine, procarbazine, altretamine, dacarbazine, mitozolomide and temozolomide.

Pharmaceutical Compositions

The invention also provides pharmaceutical compositions comprising the conjugates and fusion proteins of the invention or the compositions according to the invention. Thus, in another aspect, the invention provides a pharmaceutical composition comprising a pharmaceutically active amount of the conjugate or fusion protein according to the invention and a pharmaceutically active carrier (first pharmaceutical composition of the invention). In another aspect, the invention provides a pharmaceutical composition comprising a pharmaceutically active amount of the composition according to the invention and a pharmaceutically active carrier (second pharmaceutical composition according to the invention).

As it is used in the present invention, the expression "pharmaceutical composition" relates to a formulation that has been adapted for administering a predetermined dose of one or several therapeutic useful agents to a cell, a group of cells, an organ, a tissue or an animal in which cell division is uncontrolled, such cancer.

The first pharmaceutical composition of the invention contains a pharmaceutical effective amount of a conjugate or fusion protein according to the invention. Suitable conjugates and fusion proteins for use in the pharmaceutical compositions according to the present invention include any of the fusion proteins mentioned above under the paragraph Omomyc conjugates and fusion proteins of the invention.

The second pharmaceutical composition of the invention contains a pharmaceutical effective amount of a composition according to the invention and a pharmaceutically active carrier. The second pharmaceutical composition of the invention comprise the polypeptide of SEQ ID NO:1, a functionally equivalent variant thereof or a fusion protein according to the invention. Suitable functionally equivalent variants of the polypeptide of SEQ ID NO:1 or suitable fusion proteins for use in the second pharmaceutical compositions according to the invention are as defined above under therapeutic uses of the invention or under fusion proteins of the invention, respectively.

The expression "Pharmaceutical effective amount", as used herein, is understood as an amount capable of providing a therapeutic effect, and which can be determined by the person skilled in the art by commonly used means. The amount of the Omomyc polypeptide, of the functionally equivalent variant thereof or of the fusion protein or of the antitumoral compound that may be combined in the pharmaceutical compositions according to the invention will vary depending upon the subject and the particular mode of administration. Those skilled in the art will appreciate that dosages may also be determined with guidance from Goodman and Goldman's The Pharmacological Basis of Therapeutics, Ninth Edition (1996), Appendix II, pp. 1707-1711 and from Goodman and Goldman's The Pharmacological Basis of Therapeutics, Tenth Edition (2001), Appendix II, pp. 475-493.

The appropriate dosage of the active principle or principles within the pharmaceutical composition will depend on the type of cancer to be treated, the severity and course of the disease, whether the composition is administered for preventive or therapeutic purposes, previous therapy, the patient's clinical history and response to the peptide or polypeptide, and the discretion of the attending physician. The amount of polypeptide of SEQ ID NO:1, of the functionally equivalent variant thereof, of the fusion protein is suitably administered to the patient at one time or over a series of treatments. Depending on the type and severity of the disease, an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

In the case of the second pharmaceutical compositions according to the invention, which contain a first component selected from the polypeptide of SEQ ID NO:1, a functionally equivalent variant thereof and a fusion protein according to the invention and a second component which is an antitumoral agent, the composition may be presented as a single formulation (for example, as a tablet or a capsule comprising a fixed quantity of each one of the components) or can, on the other hand, be presented as separate formulations to be later combined for joint, sequential, or separate administration. The compositions of the invention also include the formulation as a kit-of-parts wherein the components are formulated separately but are packaged in the same container. Those skilled in the art will appreciate that the formulation of the different components in the case of the second pharmaceutical composition according to the invention may be similar, in other words, similarly formulated (in tablets or pills), which allows their administration by the same route. In the case where the different components of the invention are formulated separately, the two components can be presented in a blister. Each blister contains the drugs that must be consumed during the day. If the drugs must be administered several times a day, the drugs corresponding to each administration can be placed in different sections of the blister, preferably recording in each section of the blister the time of day when they should be administered. Alternatively, the components of the composition of the invention can be formulated differently so that the different components are differently administered. Thus, it is possible that the first component is formulated as a tablet or capsule for its oral administration and the second component is formulated for its intravenous administration or vice versa. The ratio between the components that are part of the compositions used in the second pharmaceutical composition according to the invention can be adjusted by the skilled person depending on the antitumor agent used in each particular case, as well as of the desired indication. Thus, the invention envisages compositions wherein the ratio between the quantities of the two components can range from 50:1 to 1:50, in particular from 20:1 to 1:20, from 1:10 to 10:1, or from 5:1 to 1:5.

The first and the second pharmaceutical compositions of the invention can also contain one or several additional compounds for the prevention and/or treatment of pathologies in which there is an uncontrolled cell division, such as cancer. Said additional compounds, such as antitumoral agents can form part of the pharmaceutical composition as independent entities.

The first and the second pharmaceutical compositions of the invention also contain one or several additional pharmaceutically acceptable excipients. "Pharmaceutically acceptable excipient" is understood a therapeutically inactive substance said to be used for incorporating the active ingredient and which is acceptable for the patient from a pharmacological/toxicological point of view and for the pharmaceutical chemist who manufactures it from a physical/chemical point of view with respect to the composition, formulation, stability, acceptation of the patient and bioavailability.

The number and the nature of the pharmaceutically acceptable excipients depend on the desired dosage form. The pharmaceutically acceptable excipients are known by the person skilled in the art (Faulí y Trillo C. (1993) "Tratado de Farmacia Galénica", Luzán 5, S. A. Ediciones, Madrid). Said compositions can be prepared by means of the conventional methods known in the state of the art ("Remington: The Science and Practice of Pharmacy", 20$^{th}$ edition (2003) Genaro A. R., ed., Lippincott Williams & Wilkins, Philadelphia, US).

The first and the second pharmaceutical compositions of the invention or can be administered by any type of suitable route, such as by oral route, topical route, by inhalation or parenteral route so that the pharmaceutically acceptable excipients necessary for the formulation of the desired dosage form will be included. The preferred route of administration of said pharmaceutical compositions is the endovenous route.

"Oral route" is understood as the pharmaceutical composition incorporated into the organism after deglutition. In a particular embodiment, the pharmaceutical composition of the invention can be in a dosage form suitable for its administration by oral route, whether it is solid or liquid. The dosage forms suitable for their administration by oral route can be tablets, capsules, syrups or solutions, and can contain any conventional excipient known in the art, such as binders, for example syrup, acacia, gelatin, sorbitol or polyvinylpyrrolidone; filling agents, for example lactose, sugar, corn starch, calcium phosphate, sorbitol or glycine; lubricants for compression, for example, magnesium stearate; disintegrating agents, for example starch, polyvinylpyrrolidone, sodium glycolate of starch or microcrystalline cellulose; or pharmaceutically acceptable wetting agents such as sodium lauryl sulfate. The solid oral compositions can be prepared by means of conventional processes of mixing, filling or compressing. Repetitive mixing operations can be used to completely distribute the active agent in those compositions that use high amounts of filling agents. Said operations are conventional in the art. The tablets can be prepared, for example, by means of wet or dry granulation, and optionally coating them according to the processes known in the common pharmaceutical practice, particularly with an enteric coating.

On the other hand, "topical route" is understood as an administration by non-systemic route, and includes the application of a pharmaceutical composition of the invention externally on the epidermis, in the oral cavity and the instillation of said composition into ears, eyes and nose, and in which it does not significantly enter the blood stream. "Systemic route" is understood as the administration by oral route, intravenous route, intraperitoneal route and intramuscular route. The amount of antibody required for the therapeutic or prophylactic effect will naturally vary according to the elected antibody, the nature and the severity of the illness that is going to be treated, and the patient.

"Inhalation" is understood as the administration by intranasal route and by oral inhalation. The dosage forms suitable for said administration, such as a formulation in aerosol or a meter dosed inhaler can be prepared by means of conventional techniques. In an embodiment the route of administration is the intranasal route.

As it is used herein, the term "parenteral", includes administration by intravenous route, intraperitoneal route, intramuscular route or subcutaneous route. Subcutaneous, intramuscular and intravenous dosage forms of parenteral administration are generally preferred.

In one embodiment, the first and the second pharmaceutical compositions of the invention can be adapted for their parenteral administration, such as sterile solutions, suspensions or lyophilized products in the appropriate dosage unit form. The pharmaceutical compositions suitable for its injectable use include sterile aqueous solutions (when they are soluble in water), or dispersions and sterile powders for the extemporaneous preparation of sterile injectable solutions or dispersions. For its administration by intravenous route, some suitable carriers include saline solution buffered with phosphate (PBS). In all the cases, the composition must be sterile, and must be fluid to the point which that there exists easy ability for being injected. It must be stable in the preparation and storage conditions, and must be protected from the contamination action of microorganisms such as bacteria and fungi. The carrier can be a solvent or a dispersion medium which contains, for example, water, ethanol, a pharmaceutically acceptable polyol such as glycerol, propylene glycol, liquid polyethylene glycol and suitable mixtures thereof. Suitable fluidity can be maintained, for example, by means of using a coating such as lecithin, by means of maintaining the particle size required in the case of dispersion and by means of using surfactants. The prevention of the action of the microorganisms can be achieved by means of various antibacterial and antifungal agents, for example, parabens, chlorobutanol, phenol, ascorbic acid, thiomersal, and the like. In most cases, it will be preferable to include isotonic agents, for example, sugars; polyalcohols such as mannitol, sorbitol; or sodium chloride in the composition. The prolonged absorption of the injectable compositions may be caused by the inclusion of an agent which delays the absorption, for example, aluminum and gelatin monostearate.

The injectable sterile solutions can be prepared by incorporating the active compound in the required amount in a suitable solvent with one or a combination of the aforementioned ingredients, as needed, followed by sterilization by filtration through sterile membranes. Generally, the dispersions are prepared by incorporating the active compound in a sterile vehicle containing a basic dispersion medium and the rest of the ingredients required from among those previously listed. In the case of sterile powders for the preparation of injectable sterile solutions, the preferred preparation processes are vacuum drying and lyophilization which give rise to a powder with the active ingredient plus any desired additional ingredient from a previously filtered sterile solution thereof.

The pharmaceutical compositions of the invention can be suitably administered by means of pulse infusion, for example, with decreasing doses of the composition. Preferably, the dose is administered by means of injections, more preferably intravenous or subcutaneous injections, partly depending if the administration is acute or chronic.

In one embodiment, the first or second pharmaceutical compositions of the invention are prepared with carriers which will protect said polypeptide from a rapid elimination from the body, such as a controlled release formulation, including implants and microencapsulated administration systems. Biodegradable biocompatible polymers such as ethylene vinylacetate, polyanhydrides, polyglycolic acid, collagen, polyorthoesters and polylactic acid can be used. The processes for preparing said formulations will be clear for persons skilled in the art. The materials can also be commercially obtained in Alza Corporation and Nova Pharmaceuticals, Inc.

The sustained release compositions also include preparations of antibody crystals suspended in suitable formulations which can maintain the crystals in suspension. These preparations, when they are injected by subcutaneous or intraperitoneal route may produce a sustained release effect. Other compositions also include antibodies trapped in liposomes. The liposomes containing such antibodies are prepared by means of known methods such as Epstein et al., Proc. Natl. Acad. Sci. USA, (1985) 82:3688-3692; Hwang et al., Proc. Natl. Acad. Sci. USA, (1980) 77:4030-4034; EP 52,322; EP 36,676; EP 88,046; EP 143,949.

Despite the fact that Omomyc and the conjugates and fusion proteins containing Omomyc are capable of translocating across biological membranes, the skilled person will understand that it may also be convenient to formulate the conjugates or fusion proteins comprising Omomyc in nanoparticles. The nanoparticles may contribute to preserve the integrity of the polypeptide in the biological fluids until it reaches the target organ. Moreover, in the case of compositions comprising an antitumor agent, encapsulation of the composition may decrease secondary effects caused by the antitumor agent. Lastly, nanoparticles can also be modified so as to include moieties which allow the targeting of the nanoparticule to an organ of interest.

Thus, in another embodiment, the pharmaceutical compositions of the invention comprise the conjugates, fusion proteins and compositions according to the invention forming part of a nanoparticle.

Suitable nanoparticles that can be used in the context of the present invention include such nanoscale materials as a lipid-based nanoparticle, a superparamagnetic nanoparticle, a nanoshell, a semiconductor nanocrystal, a quantum dot, a polymer-based nanoparticle, a silicon-based nanoparticle, a silica-based nanoparticle, a metal-based nanoparticle, a fullerene and a nanotube.

Targeted delivery can be achieved by the addition of ligands without compromising the ability of nanoparticles to deliver their polypeptide payloads. It is contemplated that this will enable delivery to specific cells, tissues and organs. The targeting specificity of the ligand-based delivery systems are based on the distribution of the ligand receptors on different cell types. The targeting ligand may either be non-covalently or covalently associated with a nanoparticle, and can be conjugated to the nanoparticles by a variety of methods as discussed herein.

Examples of proteins or peptides that can be used to target nanoparticles include transferin, lactoferrin, TGF-$\beta$, nerve growth factor, albumin, HIV Tat peptide, RGD peptide, and insulin, as well as others.

The first and the second pharmaceutical compositions of the invention may be formulated with a pharmaceutically acceptable carrier. In a preferred embodiment, the carrier does not allow direct delivery of the fusion protein or of the composition to the cytoplasm of the cells, i.e. the carrier is not capable of fusing with the plasmatic membrane of the target cells. As used herein "carrier" is meant any substance that serves to improve the delivery and the effectiveness of the active principle within the pharmaceutical composition. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the fusion protein or of the compositions forming part of the pharmaceutical compositions. Examples of proper carriers are well known in the literature (see for example Remington's Pharmaceutical Sciences, 19th ed., Mack Publishing Company, Easton, Pa., 1995). Examples of carriers without limitation are a series of saccharide such as lactose, dextrose, sucrose, sorbitol, mannitol, xylitol, erythritol, and maltitol; a series of starch such as corn starch, wheat starch, rice starch, and potato starch; a series of cellulose such as cellulose, methyl cellulose, sodium carboxy methyl cellulose, and hydroxyl propylmethyl cellulose; and a series of filler such as gelatin and polyvinyl pyrrolidone. In some cases, a disintegrants such as cross-linked polyvinyl pyrrolidone, agar, alginic acid, or sodium alginate may be added.

The first and the second pharmaceutical compositions of the invention are suitable for the administration into any type of mammal, preferably a human being.

The invention is detailed below by means of the following examples which are merely illustrative and by no means limiting for the scope of the invention.

EXAMPLES

Materials and Methods

Example 1

Expression of the Omomyc Construct in Rich Medium or in Minimal M9 Medium

For Omomyc production in rich medium, 1 L of 2YT medium containing ampicillin with BL21-AI™ One Shot® Chemically competent *Escherichia coli* (Life technologies) transformed with the Omomyc-pET-3a construct was inoculated, grown at 37° C. with agitation at 250 rpm until $OD_{600}$ reached 0.8. The protein expression was induced with 10 mL of Arabinose solution, incubating at 37° C. for 12 h. Alternatively, for Omomyc production in M9 minimal medium, *E. coli* transformed with the Omomyc-pET3a construct was inoculated in 1 L of M9 minimal medium containing chloramphenicol and ampicillin with BL21-CodonPlus (Strategene) and grown at 37° C. with agitation at 250 rpm until $OD_{600}$ reached 0.8. Protein expression was induced with 1 mL of IPTG 1000× solution. The cell culture was incubated with agitation at 250 rpm at 37° C. for 12 h.

The bacterial culture was centrifuged at 10,000 rpm, 4° C., 5 minutes in a SLA-1500 rotor using 250 mL bottles. The culture was centrifuged sequentially to combine the equivalent of 1 L of culture per bottle.

In order to verify the successful protein expression, 1 mL aliquot from the cultures was collected and its $OD_{600}$ was measured. 800 µL of said aliquot was spined at 16,060×g for 1 min and the supernatant was discarded. The pellet was suspended in a volume of IB Laemmli buffer equivalent to $(0.1 \times OD_{600}$ value) µL in order to ensure equal quantities of lysed cell extract in each sample and facilitate comparison between cells before and after protein expression. Then the samples were mixed by vortex, sonicated for 5 seconds at maximum power, frozen in liquid nitrogen and finally, boiled for 2 minutes (repeated 3 times) prior to loading on a denaturing 16.5% acrylamide SDS-PAGE gel. Electrophoresis was followed by Coomassie blue staining or Western blot. The IB Laemmli buffer was optimized to allow solubilization of the inclusion bodies and to ensure adequate migration and protein separation to visualize the expression of Omomyc.

Example 2

Purification of the Omomyc b-HLH-LZ

Cell pellets were suspended in 3 mL of Lysis buffer per gram of pellet by vortexing. 150 µL of Triton solution per gram of culture pellet was added. The viscosity of the suspension was reduced by sonicating on ice, at power 15 for 6×15 seconds using an ultrasonic homogenizer.

Then, the equivalent of 100 µL/g of culture pellet of bovine pancreatic DNase I was added followed by an incubation of 60 minutes at 37° C. with agitation at 50 rpm. Samples were centrifuged 20 min at 12,000×g (13,000 rpm in a SS34 rotor in a Sorvall RC 5B Plus, use 35 mL centrifuge bottles), 4° C. to pellet the inclusion bodies as well as high molecular weight complexes such as cell walls, ribosomes and non-degraded genomic DNA. Lipids, soluble proteins, amino acids, sugars and nucleic acids constitute the supernatant that was discarded after centrifugation.

The pelleted inclusion bodies ere solubilized with 15 mL of Bull cracker buffer part A by vortexing. This acidic, high ionic strength and denaturant buffer enables complete solubilization of the Omomyc construct from the inclusion bodies and allows elimination of high molecular weight complexes and residual DNA by centrifugation.

The inclusion bodies solution 1:1 was diluted with Bull cracker part B. After that, samples were centrifuged 30 min at 30,000×g (19,000 rpm in a SS34 rotor in a Sorvall RC 5B Plus) at 4° C.

The supernatant was purified by cation exchange chromatography on 5, cationic exchange columns of 5 mL (HiTrap™ SP Sepharose HP columns from GE Healthcare or the equivalent) mounted in series on a FPLC system. First, column was washed with 2 column volumes (CV) of FPLC buffer B at a flow rate of 5 mL/min. Then, the column was equilibrated with 5 CV (125 mL) of FPLC buffer A at a flow rate of 2.5 mL/min. The supernatant (equivalent to a maximum of 9 g of culture pellet per load) was loaded at 2.5 mL/min. Immediately after loading the supernatant, column was washed with 75 mL (3 CV) of U8 buffer, at a flow rate of 2.5 mL/min. Wash with 1 CV of buffer A. Then, 3 CV of 10% Buffer B was added to the column. Omomyc elution was done with a gradient of Buffer B of 10-35% in 50 mL (0.5%/mL) at 2.5 mL/min in 2.5 mL fractions. In these conditions, Omomyc eluted at ~1.5 M NaCl (i.e. ~30% v/v of the gradient) with a purity of 90%.

The fractions containing the pure construct were pooled and desalted on 5 consecutive HiTrap™ Desalting columns from GE Healthcare (or the equivalent) equilibrated with Desalting TFA buffer, at a 3.0 mL/min flow rate. The pooled fractions were injected (maximum volume of 7.5 mL per injection) and the elution was followed with $OD_{280}$ detector. The protein eluted within the first 15 mL after injection. The following fractions showing low $OD_{280}$ values and high conductivity were discarded. This method allowed ~95% recovery of 98-99% desalted protein.

The purified protein can concentrate either by centrifugation in Amicon® Ultra centrifugal filters Ultracel®-3K (Millipore™) or the equivalent, or by lyophilization. For concentration using the Amicon® Ultra, follow manufacturer's indication. Alternatively, for lyophilization, add 50% v/v acetonitrile to the desalted fractions, freeze in liquid nitrogen and lyophilize. The foamy lyophilized protein obtained can be weighted and resolubilized to 100 µl/mg in 50% v/v acetonitrile containing 0.05% v/v TFA, aliquoted 1 to 10 mg per eppendorf and lyophilized again.

Yields around 25 mg/L of culture in rich medium and 15 mg/L of culture in minimal M9 medium.

Example 3

Omomyc Transduces into A549 Cells

The authors of the invention aimed to demonstrate that cells treated with Omomyc show that, even after such a short time, Omomyc already reaches the nucleus.

Expression and purification of Omomyc was done as it is shown in Examples 1 and 2.

A549 cells (ATCC) were maintained in Dulbecco's modified Eagle's medium (DMEM) supplemented with 10% fetal bovine serum at 37° C. in a humidified atmosphere containing 5% CO2. For fluorescence microscopy, 20,000 A549 cells were seeded on 0.5 inch glass cover slips and grown for 16 hours. Fresh media supplemented with Omomyc peptide (35 µM) was added and incubated for 2 hours at 37° C. Cells were washed 3 times with PBS and fixed in 3% paraformaldehyde, and observed under the microscope.

FIG. 1 shows that Omomyc can work as a protein transduction domain transducing across the cellular membrane and translocating to the nucleus.

Example 4

Omomyc Reduces the Number of Viable A549 Cells and Induces Apoptosis

A549 cells were incubated in 24-well plates over a period of 72 hours with 10 µM Max* or Omomyc. Max* was obtained as described in Montagne M. et al. (Montagne M. et al. 2012. PLoS One, 7(2):e32172). Cells were harvested and stained with Annexin V and PI according to the manufacturer protocol (Tali® Apoptosis Kit A10788, Life technologies) and the fluorescence quantified using Tali® image-based cytometer.

Figure 2:
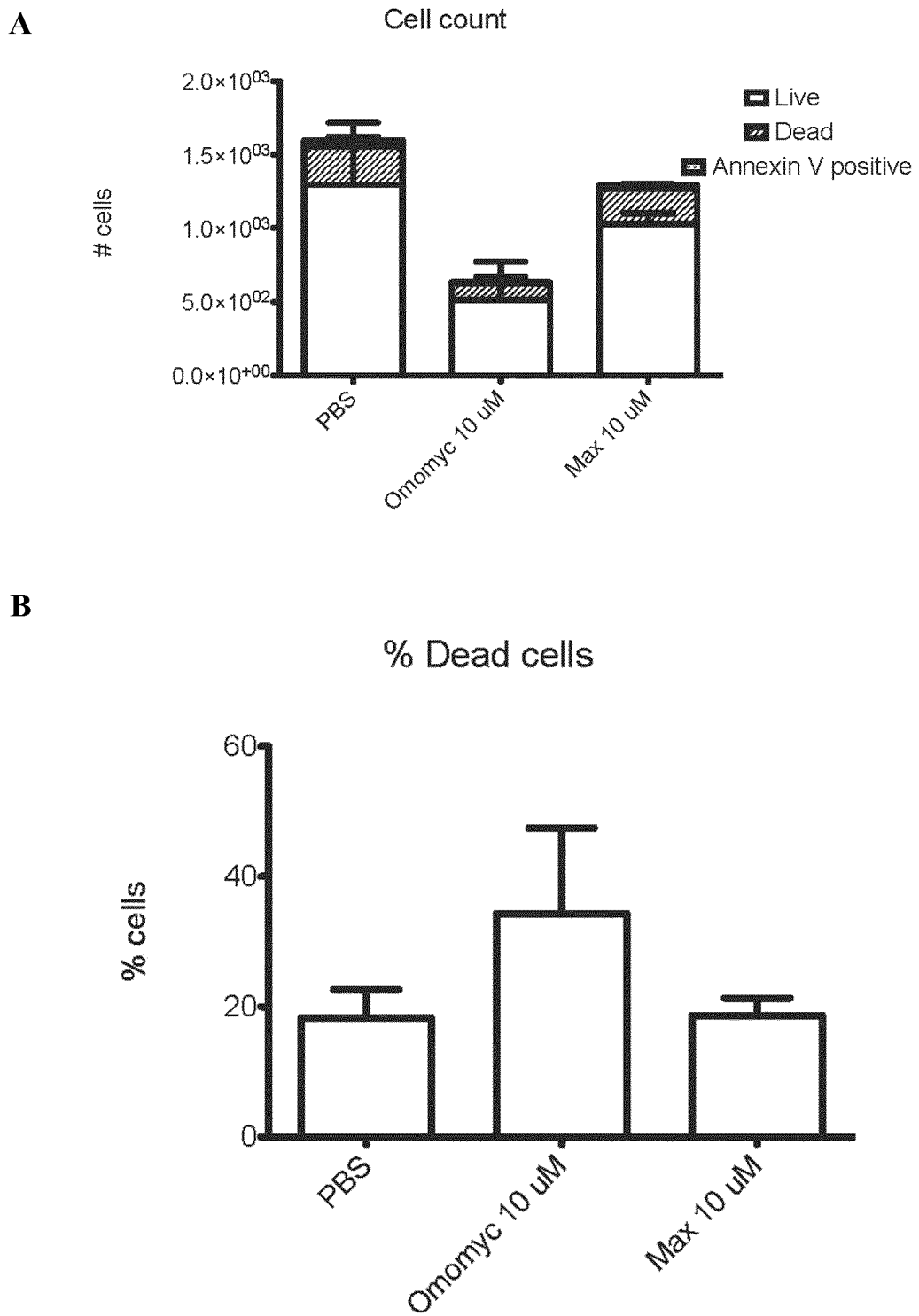
FIG. 2. Cells incubated with 10 uM of either Omomyc or Max* were counted and stained with AnnexinV and PI. (A) Total cell number of PBS, Omomyc- or Max-treated A549. (B) Percentage of dead cells stained with PI. (C) Percentage of live (non-stained) cells. (D) Percentage of AnnexinV positive cells.
Figure 2:
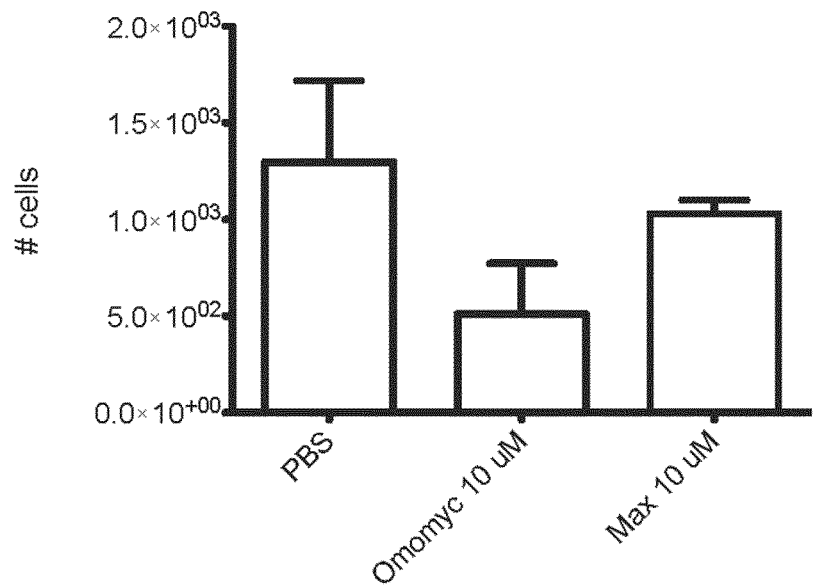
Figure 2:
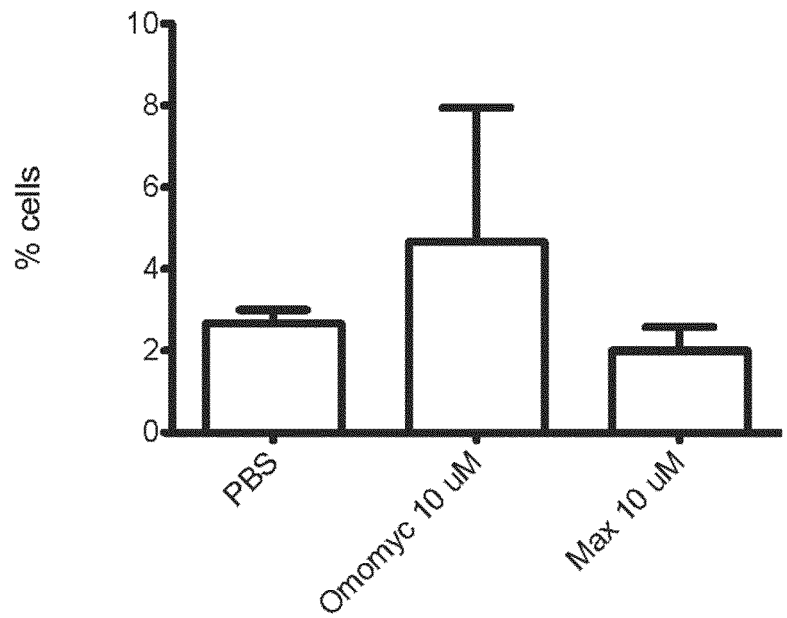

In this study the authors of the present invention show that Omomyc is more efficient at reducing the number of viable A549 cells than the bHLHZ domain of Max (FIGS. 2 A and C). Consistently, the percentage of dead/apoptotic cells is higher upon treatment with the Omomyc peptide than with the Max* peptide (FIGS. 2B and D).

Example 5

Omomyc is More Folded than c-Myc* and More Thermally Stable than Both Max* and c-Myc* in Solution.

Thermally stable polypeptides are advantageous in those circumstances when the polypeptide has to be formulated as a pharmaceutical composition. Hence, the comparative thermal stability of Omomyc and Max* were determined.

The Omomyc gene was expressed as described in Example 1 and purified as in Example 2 above. The purification of Max* was carried out as described in detail in Beaulieu M. E. et al., 2013 (Methods Mol Biol, 1012:7-20). Briefly, BL21-DE3-pLys bacteria were transformed with a pET-3a expression vector containing the Max* insert, and cultured as described above. Induction was carried out with IPTG (0.6 mM) for 4 hours, after which cells were harvested. After lysis with the Lysis buffer and centrifugation at 30000×g, the solubilized protein extract was purified using cation-exchange chromatography and desalted as described above. The purified and lyophilized proteins were resuspended in 50 mM $KH_2PO_4$, 50 mM KCl, 5 mM DTT (pH was adjusted using 1N KOH or 1N HCl).

Figure 3:
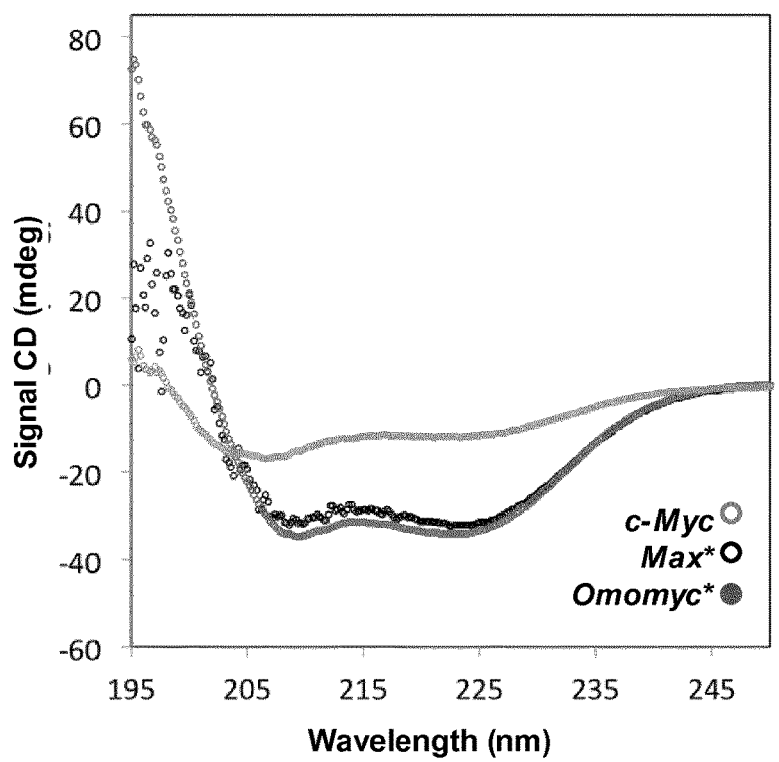
FIG. 3. (A) Circular dichroism (CD) spectra recorded at 20° C. for c-Myc*, Max* and Omomyc purified proteins (32 µM) showing that Omomyc has a folded structure more similar to that of Max* than Myc*. (mdeg, millidegrees) (B) Thermal denaturation studied by circular dichroism at 1° C./min for c-Myc*, Max* and Omomyc purified proteins showing that Omomyc has a folded structure more thermally stable than that of Max*. (° m, millidegrees at the specified wavelength of 222 nm).
Figure 3:
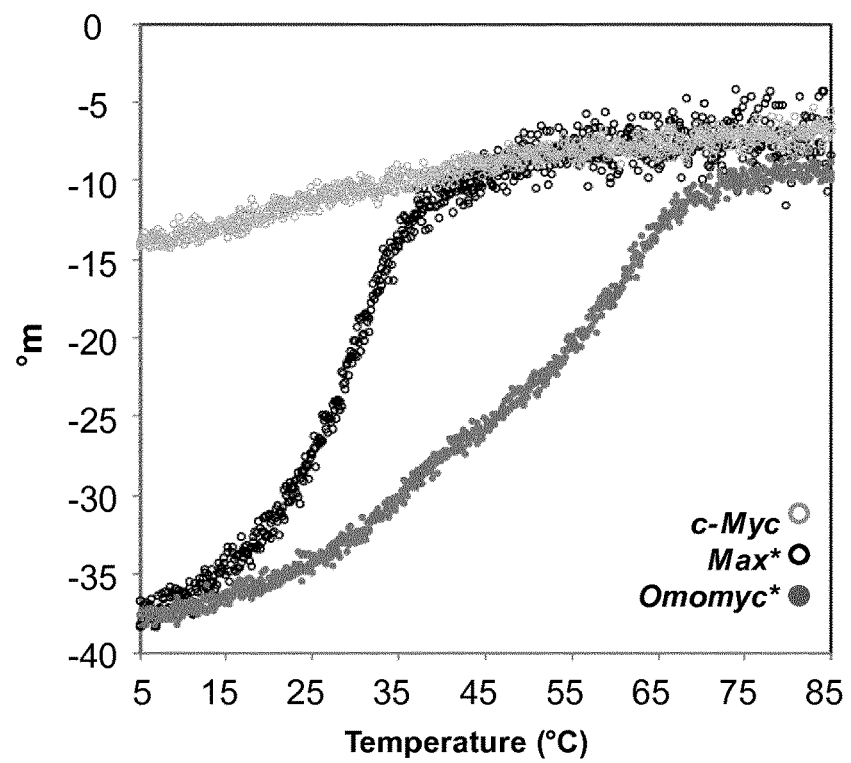

Circular dichroism measurements were performed as described in Beaulieu M. E. et al., 2012 (J Mol Recognit, 25(7):414-26), using a protein concentration of 32 µM. The CD spectra were recorded at 20° C. and the thermal denaturation was performed at 1° C./min (FIGS. 3A and 3B), monitoring at a wavelength of 222 nm to measure the helical content (reflecting the folded, structured state) of the protein.

Example 6

Omomyc Penetrates Nuclei of Cells More Efficiently than Max*

Figure 4:
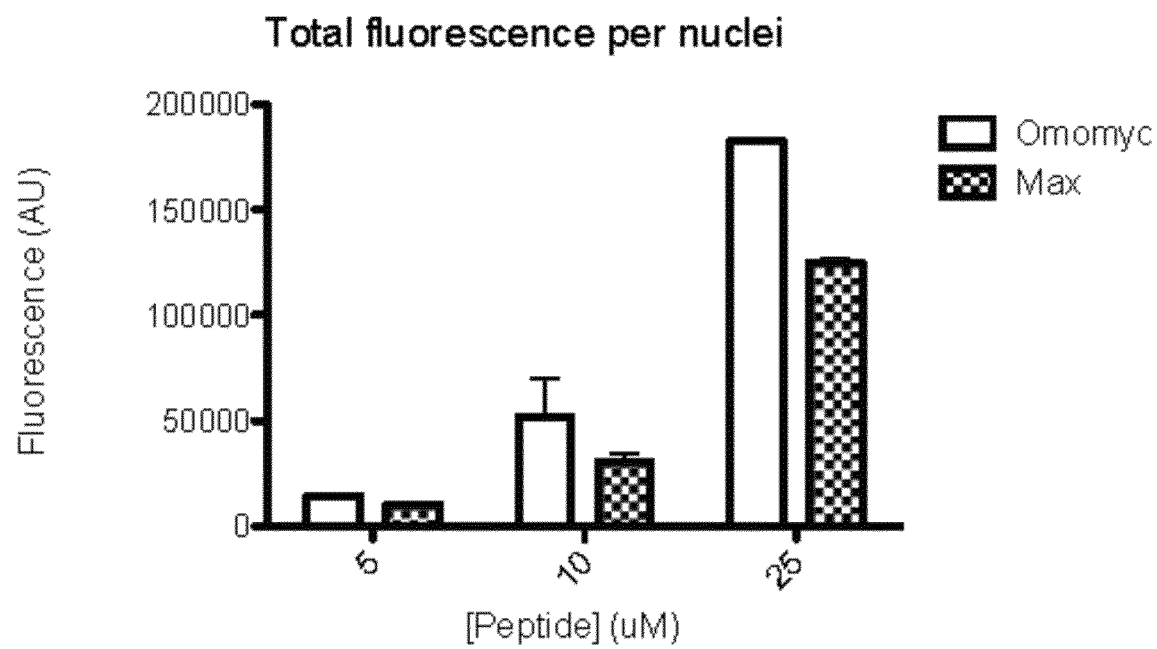
FIG. 4. Quantification of fluorescence from confocal microscopy images of A549 cells fixed with 4% PFA after 2 hours of incubation at 37° C. with Omomyc or Max* at different peptide concentrations (5, 10 and 25 µM) (30-80 cells counted per image). AU, arbitrary units.

Briefly, the purified Omomyc and Max* peptides were labelled with fluorescein-maleimide (FITC) through an engineered C-terminal cysteine residue. After purification and assessment of the presence of a single fluorescent label per protein molecule by mass spectrometry, different concentrations of protein (5 µM, 10 µM or 25 µM) were added to A549 cells (K-Ras mutant lung adenocarcinoma) cultured in RPMI containing 0.5% serum and incubated for 2 h at 37° C. before being washed thrice with PBS and fixed in 4% PFA for 10 min, stained with 1.5 µg/mL Hoechst for 10 min and mounted on microscopy slides. The confocal microscopy images showed that Omomyc penetrates the nuclei of A549 cells more efficiently than Max* at concentrations of 5, 10 and 25 µM (data not shown). Nuclear fluorescence intensity was quantified using ImageJ, with 30 to 80 cells counted per image. The quantification of the cell penetration observed for Omomyc and Max* in A549 fixed cells is shown in FIG. 4.

Figure 5:
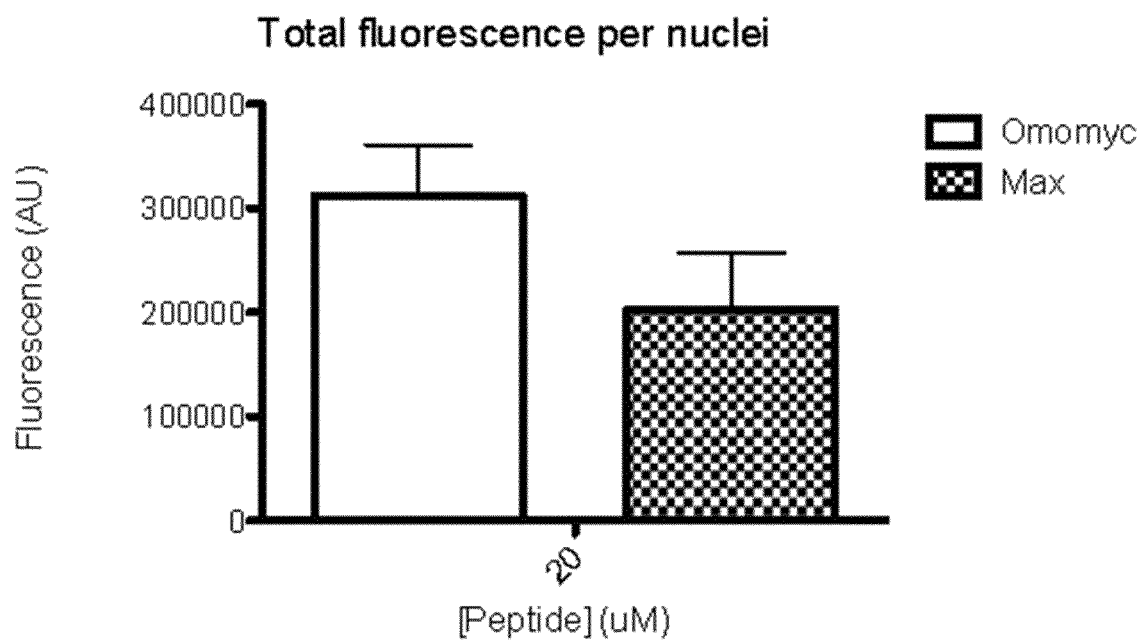
FIG. 5. Quantification of fluorescence from confocal microscopy images of A549 live cells after 20 minutes of incubation at 37° C. with Omomyc or Max* (20 µM). AU, arbitrary units.

The superior cell penetrating ability of Omomyc over Max* was confirmed at a concentration of 20 µM in live cells (to avoid potential artifacts of fixation) after 20 minutes of incubation. Briefly, the FITC-labelled Omomyc and Max* were added to A549 culture cells in RPMI containing 0.5% serum and incubated for 20 minutes at 37° C. before being washed thrice in PBS and mounted with Hoechst-containing mounting media. The confocal microscopy images showed that Omomyc penetrates the nuclei of A549 live cells more efficiently than Max* at 20 µM (data not shown). Nuclear fluorescence intensity was quantified using ImageJ, with 30 to 80 cells counted per image. The quantification of the cell penetration observed for Omomyc and Max* in A549 live cells is shown in FIG. 5.

Example 7

Omomyc Entry Occurs Through an ATP-Dependent Process

Max* was shown to penetrate cells through an ATP-dependent process, which can be blocked lowering the temperature at 4° C. A similar mechanism is involved in Omomyc's cell penetrating ability. A549 cells were incubated for 2 hours with 20 µM FITC-labelled peptide at 4° C. and fixed with 4% PFA, before being washed thrice with PBS and mounted on microscopy slides using Hoechst-containing mounting media. Confocal microscopy images showed that Omomyc entry can be blocked lowering the temperature at 4° C.

Example 8

Omomyc Reduces the Total Number of Cells More Efficiently than Max*

Figure 6:
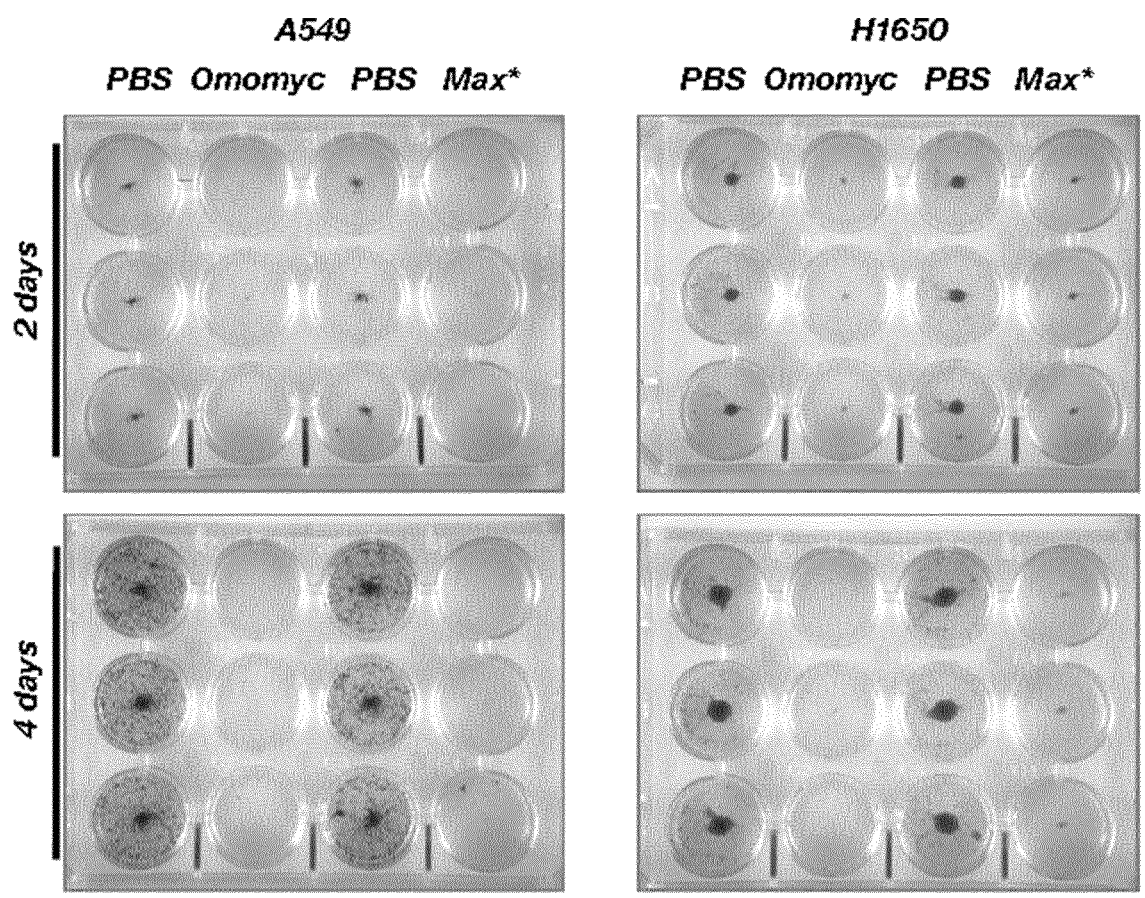
FIG. 6. Crystal violet staining of A549 and H1650 lung adenocarcinoma cells treated with 25 µM Omomyc or Max* peptide for the indicated times.
Figure 7:
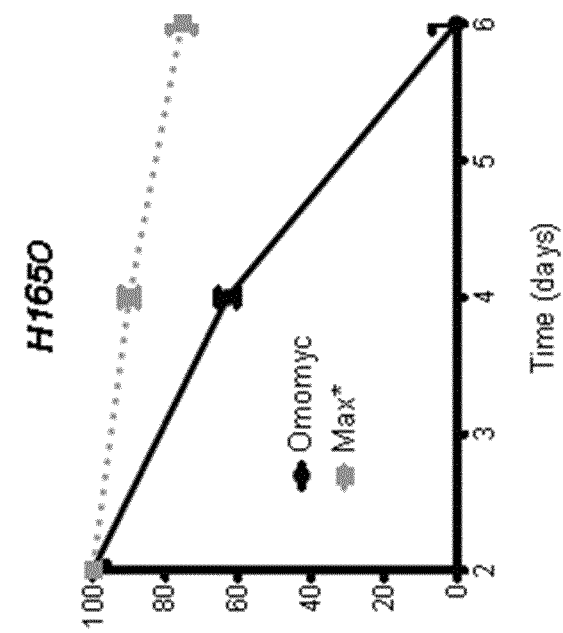
FIG. 7. Quantification of the inhibition of proliferation by crystal violet staining of A549 and H1650 lung adenocarcinoma cells treated with 25 µM Omomyc or Max* peptides for the indicated times.
Figure 7:
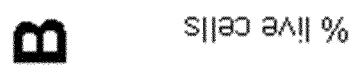
Figure 7:
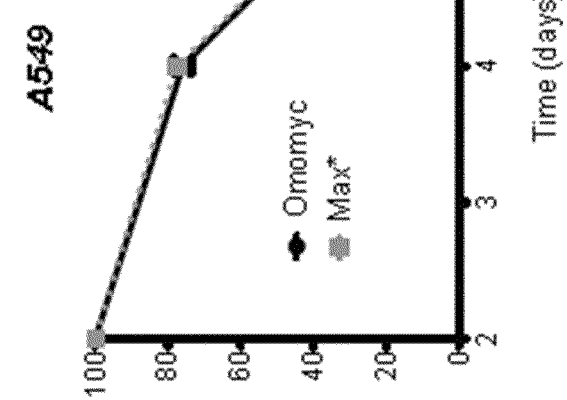
Figure 7:

Briefly, A549 and H1650 lung adenocarcinoma cells were incubated with 25 µM Omomyc or Max* peptides in RPMI containing 5% serum and fixed at the indicated time (2 days or 4 days) with 4% PFA followed by crystal violet staining (0.5% crystal violet in 25% methanol for 10 minutes) and washing at least three times with water. Both Omomyc and Max* prevent growth of cells, but Omomyc is more efficient in doing so (FIG. 6). The crystal violet stained cells were dissolved in 10% acetic acid and the resulting solution was diluted 1:4 in $H_2Odd$ and quantified by measuring absorbance at $OD_{595}$. Quantification of the inhibition of proliferation by crystal violet showed that Omomyc is clearly more efficient than Max* to reduce proliferation of H1650 cells (EGFR-mutant lung adenocarcinoma cells) when used at 25 µM concentration over 6 days (FIG. 7).

Figure 8:
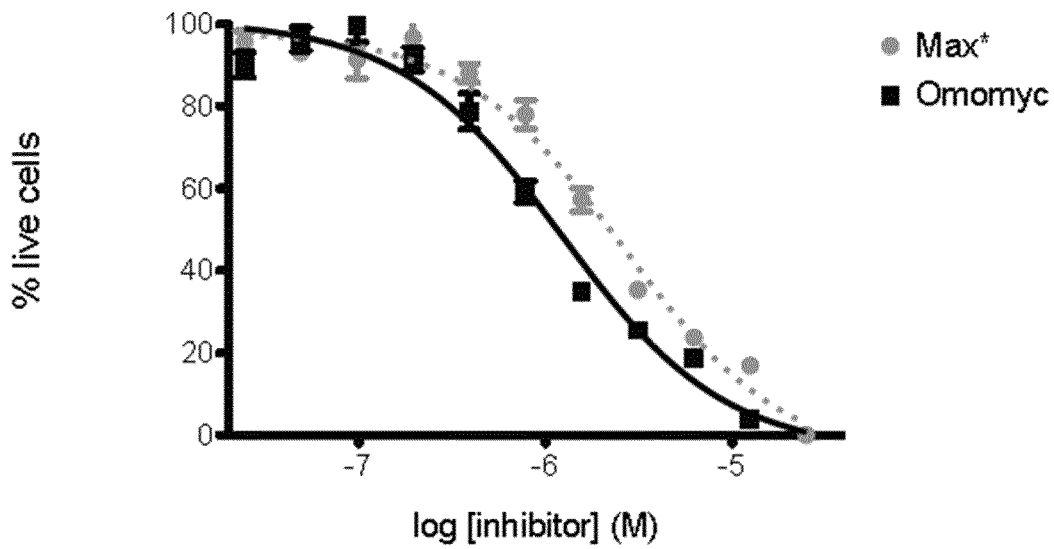
FIG. 8. Dose response of A549 cells to Omomyc and Max* by crystal violet staining quantification.

In order to calculate the $IC_{50}$ of Omomyc and Max, A549 cells were treated with the indicated peptide concentration in culture media containing 5% serum and stained with crystal violet as described above. Quantification was performed as described above. FIG. 8 shows dose response of A549 cells to Omomyc versus Max* showing that Omomyc has a lower IC$_{50}$ than Max* (i.e. Omomyc needs a lower dose compared to Max* in order to reduce the number of cells to a half). Specifically, IC$_{50}$ for Omomyc is 1.2 µM and IC$_{50}$ for Max* is 2.6 µM.

Figure 9:
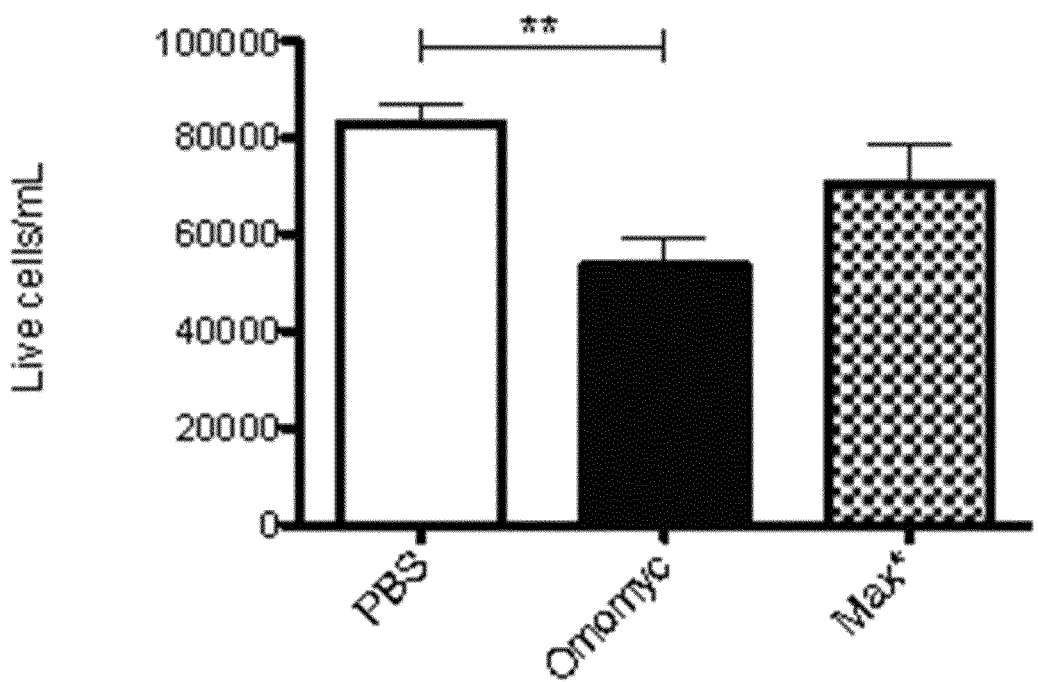
FIG. 9. Quantification of proliferation of U87 glioma cells treated with Omomyc or Max* peptides at 25 µM.

The effect of Omomyc on proliferation of cells was assayed in U87 glioma cells. U87 glioma cells were incubated with Omomyc or Max* peptides (25 µM final concentration) in DMEM containing 5% serum for 48 h. Cells were trypsinized and counted using Tali cell counter (Life technologies Inc.). FIG. 9 shows that Omomyc reduces the proliferation of U87 glioma cells more efficiently than Max*.

Example 9

Figure 10:
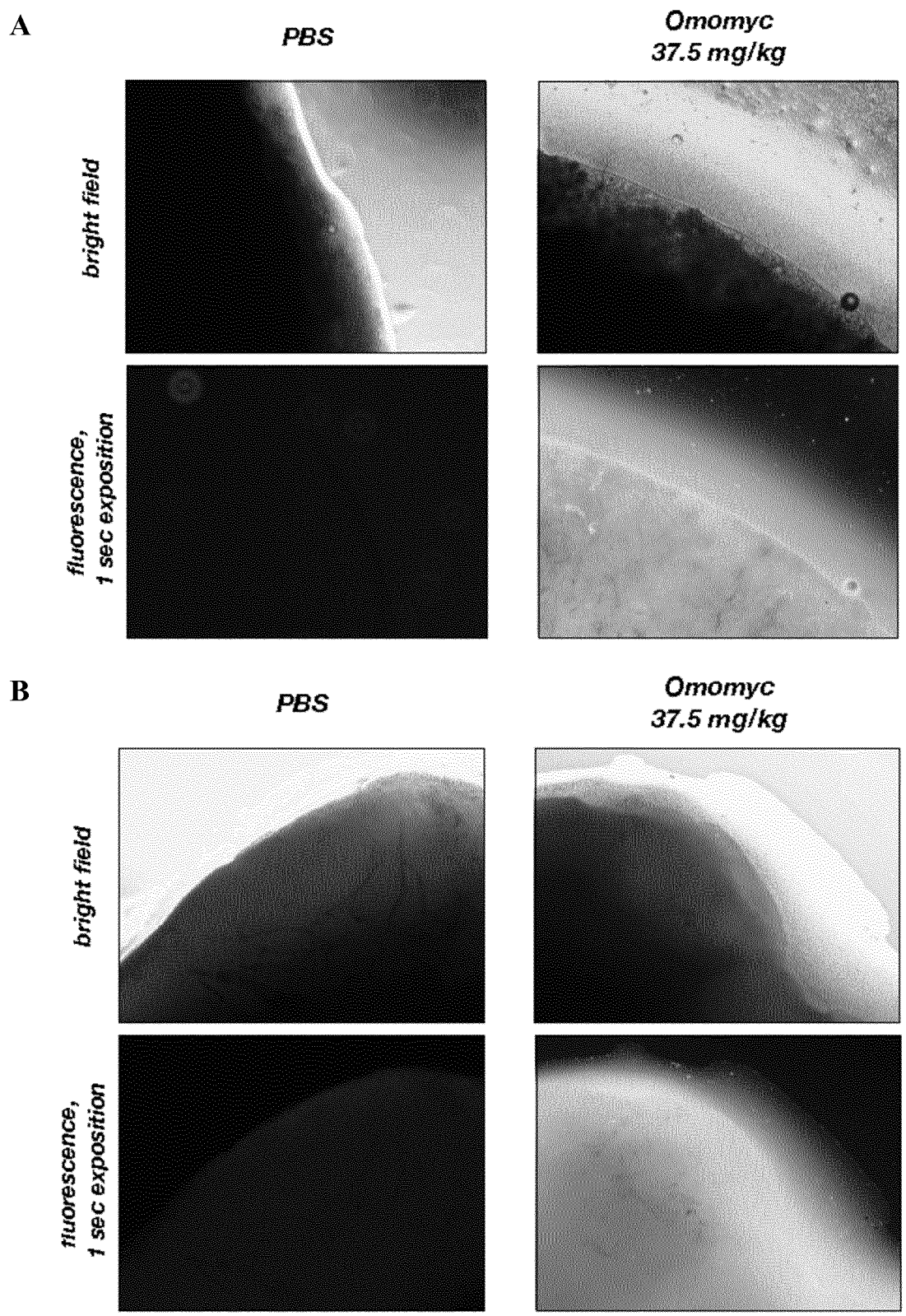
FIG. 10. (A) Lung of untreated (left) and treated (right) animals 10 minutes after intranasal administration of the fluorescent peptide Omomyc (single dose of 37.5 mg/kg). (B) Brain of untreated (left) and treated (right) animals 10 minutes after intranasal administration of the fluorescent peptide Omomyc (single dose of 37.5 mg/kg).

Omomyc Efficiently Reaches Lung and Brain Tissue after Intranasal Administration Animals were treated with a single dose of 37.5 mg/kg of Omomyc or left untreated (treated with PBS) by intranasal administration. 10 minutes after intranasal administration the fluorescent peptide was detected. The lung of the treated animals appears fluorescent as a consequence of Omomyc localization (FIG. 10A). This demonstrates that the Omomyc peptide can be administered to animals by intranasal instillation and it efficiently reaches the lung. The brain of the same animals described in the previous figure also appears fluorescent (FIG. 10B). It is apparent that the fluorescent Omomyc peptide can pass the blood-brain barrier (BBB) and reach the brain.

Example 10

Omomyc Peptide has a Therapeutic Effect In Vivo

Figure 11:
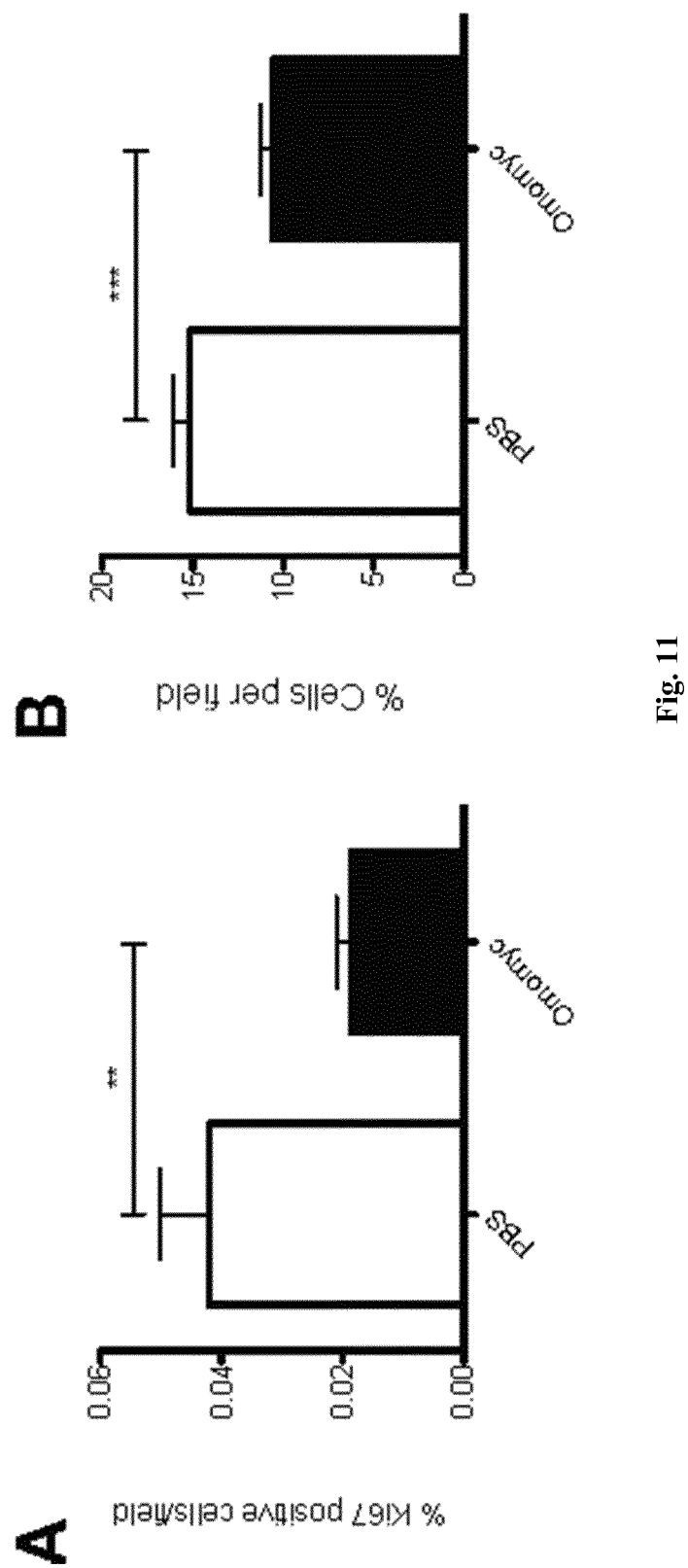
FIG. 11. Treatment of lung adenocarcinoma with PBS or with Omomyc by intranasal administration. (A) Proliferative rate of tumors. (B) Cellular density.

Administered as a peptide intranasally, Omomyc reduces proliferation in a KRas-driven lung adenocarcinoma mouse model. The inventors made use of a mouse model of KRas driven tumorigenesis (the LSLKRasG12D model). Briefly, 8 weeks old mice were instillated with an AdenoCre virus to induce expression of the KRas-G12D mutant protein specifically in the lungs. When the mice developed lung adenocarcinoma (18 weeks after infection), the animals were treated intranasally with the Omomyc peptide (15 mg/kg in 35 µL volume) daily for 3 days. Omomyc reduced the proliferative rate of tumors (Ki67 staining; FIG. 11A) and reduced cellular density (FIG. 11B).

Figure 12:
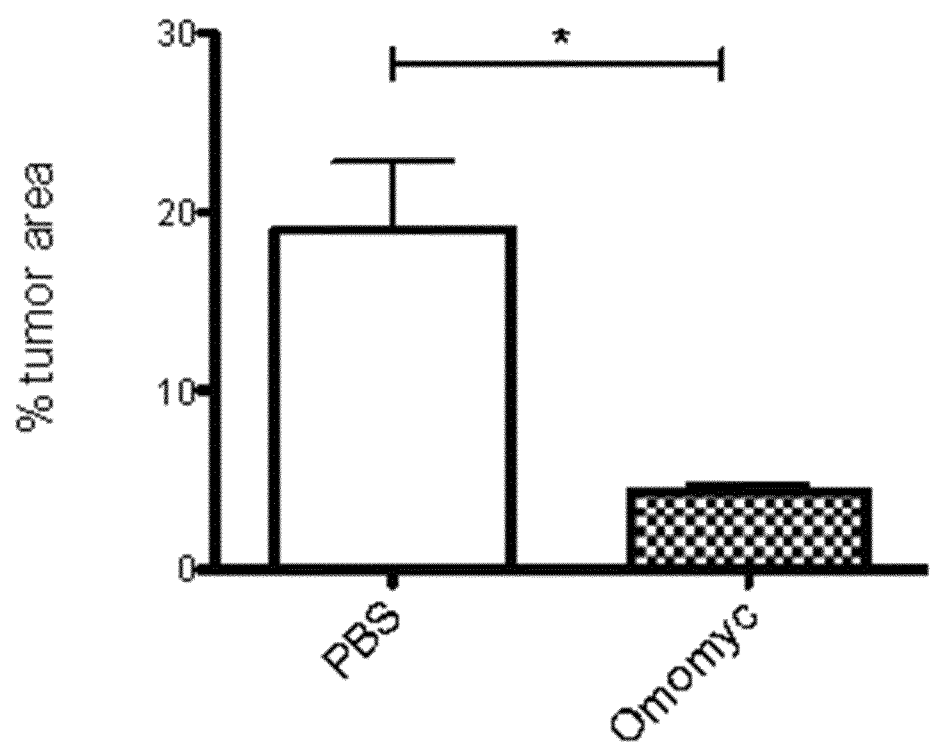
FIG. 12. Measurement of the % tumor area after treatment of lung adenocarcinoma with PBS or with Omomyc by intranasal administration.

The Omomyc peptide also reduces tumor burden in vivo after 1 week treatment. Using the same mouse model and experimental conditions as described previously, the animals were treated daily for 1 week with 15 mg/kg of peptide. The % tumor area was measured using ImageJ. FIG. 12 shows that Omomyc reduces tumor burden in a KRas-driven lung adenocarcinoma mouse model.

The invention claimed is:

1. A method for treating cancer comprising administering to a subject in need thereof a therapeutically effective amount of a polypeptide of SEQ ID NO: 1 or a functionally equivalent variant thereof having a degree of identity with respect to SEQ ID NO: 1 greater than 60%, wherein the method does not involve the administration of the nucleic acid encoding the polypeptide of SEQ ID NO: 1 or the functionally equivalent variant thereof.

2. The method according to claim 1, wherein the cancer is colon cancer, rectal cancer, lung cancer, breast cancer or brain cancer.

3. The method according to claim 1, wherein the cancer is Myc-induced cancer.

4. The method according to claim 1, wherein the cancer is a cancer associated with a mutation in the KRAS gene.

5. The method according to claim 4, wherein the mutation in the KRAS gene is a mutation at the glycine at position 12, at the glycine at position 13, or at the glutamine at position 61.

6. The method according to claim 4, wherein the mutation in the KRAS gene is selected from the group consisting of the G12S mutation, the G12V mutation, the G13D mutation, the G12C mutation, the G12R mutation, the G12F mutation, the G12I mutation, the G13C mutation, the G13R mutation, or the Q61L mutation.

7. The method according to claim 1, wherein the functionally equivalent variant of the polypeptide of SEQ ID NO: 1 has a degree of identity with respect to SEQ ID NO: 1 greater than 70%, 80%, 90%, 91%, 92%, 93%, 94%, 95%, 96%, 97%, 98% or 99%.

8. The method according to claim 1, wherein the functionally equivalent variant of the polypeptide of SEQ ID NO: 1 is a polypeptide which results from a deletion, insertion, and/or addition of one or more amino acids with respect to the polypeptide of SEQ ID NO: 1, and/or from a conservative substitution of one or more amino acids with respect to the polypeptide of SEQ ID NO: 1.

9. The method according to claim 1, wherein the polypeptide is administered via intravenous route, endovenous route or intranasal route.

10. The method according to claim 1, wherein the functionally equivalent variant of the polypeptide of SEQ ID NO: 1 consists essentially of the polypeptide of SEQ ID NO: 1.

11. The method according to claim 1, wherein the functionally equivalent variant of the polypeptide of SEQ ID NO: 1 is a polypeptide showing an activity of at least 60%, 70%, 80%, 90% or 100% of the polypeptide of SEQ ID NO: 1.

12. The method according to claim 1, further comprising administering a pharmaceutically acceptable excipient.

13. The method according to claim 1, further comprising administering an antitumoral agent.

14. The method according to claim 13, wherein the antitumoral agent is selected from the group consisting of paclitaxel, cisplatin, doxorubicin and temozolomide.

15. A method for treating colon cancer, rectal cancer, lung cancer, breast cancer or brain cancer, comprising administering to a subject in need thereof a therapeutically effective amount of a functionally equivalent variant of SEQ ID NO: 1 having a degree of identity with respect to SEQ ID NO: 1 greater than 98%, wherein the functionally equivalent variant results from an addition of one amino acid with respect to SEQ ID NO: 1, and wherein the method does not involve the administration of the nucleic acid encoding the polypeptide of SEQ ID NO: 1 or the functionally equivalent variant thereof.

16. The method according to claim 15, wherein the functionally equivalent variant is administered via intravenous route.

17. The method according to claim 15, wherein the functionally equivalent variant is administered via pulse infusion.

18. The method according to claim 15, wherein the functionally equivalent variant is SEQ ID NO: 1 with a methionine added at the N-terminal end.

19. A method for treating a Myc-induced cancer or a cancer associated with a mutation in the KRAS gene, comprising administering to a subject in need thereof a therapeutically effective amount of a functionally equivalent variant of SEQ ID NO: 1 having a degree of identity with respect to SEQ ID NO: 1 greater than 98%, wherein the functionally equivalent variant results from an addition of one amino acid with respect to SEQ ID NO: 1, and wherein the method does not involve the administration of the nucleic acid encoding Omomyc or the functionally equivalent variant thereof.

20. The method according to claim 19, wherein the mutation in the KRAS gene is a mutation at the glycine at position 12, at the glycine at position 13, or at the glutamine at position 61.

21. The method according to claim 19, wherein the mutation in the KRAS gene is selected from the group consisting of the G12S mutation, the G12V mutation, the G13D mutation, the G12C mutation, the G12R mutation, the G12F mutation, the G12I mutation, the G13C mutation, the G13R mutation, or the Q61L mutation.

22. The method according to claim 19, wherein the functionally equivalent variant is administered via intravenous route.

23. The method according to claim 19, wherein the functionally equivalent variant is SEQ ID NO: 1 with a methionine added at the N-terminal end.

* * * * *

SEQUENCE LISTING

```
<160> NUMBER OF SEQ ID NOS: 57

<210> SEQ ID NO 1
<211> LENGTH: 90
<212> TYPE: PRT
<213> ORGANISM: Artificial Sequence
<220> FEATURE:
<223> OTHER INFORMATION: OMOMYC

<400> SEQUENCE: 1

Thr Glu Glu Asn Val Lys Arg Arg Thr His Asn Val Leu Glu Arg Gln
1               5                   10                  15

Arg Arg Asn Glu Leu Lys Arg Ser Phe Phe Ala Leu Arg Asp Gln Ile
            20                  25                  30

Pro Glu Leu Glu Asn Asn Glu Lys Ala Pro Lys Val Val Ile Leu Lys
        35                  40                  45

Lys Ala Thr Ala Tyr Ile Leu Ser Val Gln Ala Glu Thr Gln Lys Leu
    50                  55                  60

Ile Ser Glu Ile Asp Leu Leu Arg Lys Gln Asn Glu Gln Leu Lys His
65                  70                  75                  80

Lys Leu Glu Gln Leu Arg Asn Ser Cys Ala
                85                  90

<210> SEQ ID NO 2
<211> LENGTH: 454
<212> TYPE: PRT
<213> ORGANISM: Homo sapiens

<400> SEQUENCE: 2

Met Asp Phe Phe Arg Val Val Glu Asn Gln Gln Pro Pro Ala Thr Met
1               5                   10                  15

Pro Leu Asn Val Ser Phe Thr Asn Arg Asn Tyr Asp Leu Asp Tyr Asp
            20                  25                  30

Ser Val Gln Pro Tyr Phe Tyr Cys Asp Glu Glu Glu Asn Phe Tyr Gln
        35                  40                  45
```

```
Gln Gln Gln Gln Ser Glu Leu Gln Pro Pro Ala Pro Ser Glu Asp Ile
         50                  55                  60

Trp Lys Lys Phe Glu Leu Leu Pro Thr Pro Pro Leu Ser Pro Ser Arg
 65                  70                  75                  80

Arg Ser Gly Leu Cys Ser Pro Ser Tyr Val Ala Val Thr Pro Phe Ser
                     85                  90                  95

Leu Arg Gly Asp Asn Asp Gly Gly Gly Ser Phe Ser Thr Ala Asp
                100                 105                 110

Gln Leu Glu Met Val Thr Glu Leu Leu Gly Gly Asp Met Val Asn Gln
            115                 120                 125

Ser Phe Ile Cys Asp Pro Asp Glu Thr Phe Ile Lys Asn Ile Ile
        130                 135                 140

Ile Gln Asp Cys Met Trp Ser Gly Phe Ser Ala Ala Lys Leu Val
145                 150                 155                 160

Ser Glu Lys Leu Ala Ser Tyr Gln Ala Ala Arg Lys Asp Ser Gly Ser
                165                 170                 175

Pro Asn Pro Ala Arg Gly His Ser Val Cys Ser Thr Ser Ser Leu Tyr
                180                 185                 190

Leu Gln Asp Leu Ser Ala Ala Ser Glu Cys Ile Asp Pro Ser Val
    195                 200                 205

Val Phe Pro Tyr Pro Leu Asn Asp Ser Ser Ser Pro Lys Ser Cys Ala
210                 215                 220

Ser Gln Asp Ser Ser Ala Phe Ser Pro Ser Ser Asp Ser Leu Leu Ser
225                 230                 235                 240

Ser Thr Glu Ser Ser Pro Gln Gly Ser Pro Glu Pro Leu Val Leu His
                245                 250                 255

Glu Glu Thr Pro Pro Thr Thr Ser Ser Asp Ser Glu Glu Gln Glu
                260                 265                 270

Asp Glu Glu Glu Ile Asp Val Val Ser Val Glu Lys Arg Gln Ala Pro
        275                 280                 285

Gly Lys Arg Ser Glu Ser Gly Ser Pro Ser Ala Gly Gly His Ser Lys
        290                 295                 300

Pro Pro His Ser Pro Leu Val Leu Lys Arg Cys His Val Ser Thr His
305                 310                 315                 320

Gln His Asn Tyr Ala Ala Pro Pro Ser Thr Arg Lys Asp Tyr Pro Ala
                325                 330                 335

Ala Lys Arg Val Lys Leu Asp Ser Val Arg Val Leu Arg Gln Ile Ser
                340                 345                 350

Asn Asn Arg Lys Cys Thr Ser Pro Arg Ser Ser Asp Thr Glu Glu Asn
            355                 360                 365

Val Lys Arg Arg Thr His Asn Val Leu Glu Arg Gln Arg Arg Asn Glu
    370                 375                 380

Leu Lys Arg Ser Phe Phe Ala Leu Arg Asp Gln Ile Pro Glu Leu Glu
385                 390                 395                 400

Asn Asn Glu Lys Ala Pro Lys Val Val Ile Leu Lys Lys Ala Thr Ala
                405                 410                 415

Tyr Ile Leu Ser Val Gln Ala Glu Glu Gln Lys Leu Ile Ser Glu Glu
                420                 425                 430

Asp Leu Leu Arg Lys Arg Arg Glu Gln Leu Lys His Lys Leu Glu Gln
            435                 440                 445

Leu Arg Asn Ser Cys Ala
    450
```

```
<210> SEQ ID NO 3
<211> LENGTH: 273
<212> TYPE: DNA
<213> ORGANISM: Artificial Sequence
<220> FEATURE:
<223> OTHER INFORMATION: polynucleotide encoding OMOMYC

<400> SEQUENCE: 3
accgaggaga atgtcaagag gcgaacacac aacgtcttgg agcgccagag gaggaacgag      60
ctaaaacgga gcttttttgc cctgcgtgac cagatcccgg agttggaaaa caatgaaaag     120
gcccccaagg tagttatcct taaaaaagcc acagcataca tcctgtccgt ccaagcagag     180
acgcaaaagc tcatttctga aatcgacttg ttgcggaaac aaaacgaaca gttgaaacac     240
aaacttgaac agctacggaa ctcttgtgcg taa                                  273

<210> SEQ ID NO 4
<211> LENGTH: 16
<212> TYPE: PRT
<213> ORGANISM: Artificial Sequence
<220> FEATURE:
<223> OTHER INFORMATION: CPP sequence found in Drosophila antennapedia
      protein

<400> SEQUENCE: 4

Arg Gln Ile Lys Ile Trp Phe Gln Asn Arg Arg Met Lys Trp Lys Lys
1               5                   10                  15

<210> SEQ ID NO 5
<211> LENGTH: 34
<212> TYPE: PRT
<213> ORGANISM: Artificial Sequence
<220> FEATURE:
<223> OTHER INFORMATION: CPP sequence found in the herpesvirus simplex 1
      (HSV-1) VP22 DNA-binding protein

<400> SEQUENCE: 5

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Glu

<210> SEQ ID NO 6
<211> LENGTH: 24
<212> TYPE: PRT
<213> ORGANISM: Artificial Sequence
<220> FEATURE:
<223> OTHER INFORMATION: CPP  sequence of Bac-7

<400> SEQUENCE: 6

Arg Arg Ile Arg Pro Arg Pro Pro Arg Leu Pro Arg Pro Arg Pro Arg
1               5                   10                  15

Pro Leu Pro Phe Pro Arg Pro Gly
            20

<210> SEQ ID NO 7
<211> LENGTH: 9
<212> TYPE: PRT
<213> ORGANISM: Artificial Sequence
<220> FEATURE:
<223> OTHER INFORMATION: CPP sequence of the HIV-1 TAT protein  (amino
      acids 49-57)

<400> SEQUENCE: 7
```

```
Arg Lys Lys Arg Arg Gln Arg Arg
1               5

<210> SEQ ID NO 8
<211> LENGTH: 13
<212> TYPE: PRT
<213> ORGANISM: Artificial Sequence
<220> FEATURE:
<223> OTHER INFORMATION: CPP sequence of the HIV-1 TAT protein (amino
      acids 48-60)

<400> SEQUENCE: 8

Gly Arg Lys Lys Arg Arg Gln Arg Arg Arg Thr Pro Gln
1               5                   10

<210> SEQ ID NO 9
<211> LENGTH: 11
<212> TYPE: PRT
<213> ORGANISM: Artificial Sequence
<220> FEATURE:
<223> OTHER INFORMATION: CPP sequence of the HIV-1 TAT protein (amino
      acids 47-57)

<400> SEQUENCE: 9

Tyr Gly Arg Lys Lys Arg Arg Gln Arg Arg Arg
1               5                   10

<210> SEQ ID NO 10
<211> LENGTH: 20
<212> TYPE: PRT
<213> ORGANISM: Artificial Sequence
<220> FEATURE:
<223> OTHER INFORMATION: CPP sequence of S413-PV peptide

<400> SEQUENCE: 10

Ala Leu Trp Lys Thr Leu Leu Lys Lys Val Leu Lys Ala Pro Lys Lys
1               5                   10                  15

Lys Arg Lys Val
            20

<210> SEQ ID NO 11
<211> LENGTH: 15
<212> TYPE: PRT
<213> ORGANISM: Artificial Sequence
<220> FEATURE:
<223> OTHER INFORMATION: CPP sequence of penetratin

<400> SEQUENCE: 11

Arg Gln Ile Lys Trp Phe Gln Asn Arg Arg Met Lys Trp Lys Lys
1               5                   10                  15

<210> SEQ ID NO 12
<211> LENGTH: 18
<212> TYPE: PRT
<213> ORGANISM: Artificial Sequence
<220> FEATURE:
<223> OTHER INFORMATION: CPP  sequence of SynB1

<400> SEQUENCE: 12

Arg Gly Gly Arg Leu Ser Tyr Ser Arg Arg Arg Phe Ser Thr Ser Thr
1               5                   10                  15

Gly Arg

<210> SEQ ID NO 13
<211> LENGTH: 10
```

```
-continued

<212> TYPE: PRT
<213> ORGANISM: Artificial Sequence
<220> FEATURE:
<223> OTHER INFORMATION: CPP sequence of SynB3

<400> SEQUENCE: 13

Arg Arg Leu Ser Tyr Ser Arg Arg Arg Phe
1               5                   10

<210> SEQ ID NO 14
<211> LENGTH: 12
<212> TYPE: PRT
<213> ORGANISM: Artificial Sequence
<220> FEATURE:
<223> OTHER INFORMATION: CPP sequence of PTD-4

<400> SEQUENCE: 14

Pro Ile Arg Arg Arg Lys Lys Leu Arg Arg Leu Lys
1               5                   10

<210> SEQ ID NO 15
<211> LENGTH: 12
<212> TYPE: PRT
<213> ORGANISM: Artificial Sequence
<220> FEATURE:
<223> OTHER INFORMATION: CPP sequence of PTD-5

<400> SEQUENCE: 15

Arg Arg Gln Arg Arg Thr Ser Lys Leu Met Lys Arg
1               5                   10

<210> SEQ ID NO 16
<211> LENGTH: 15
<212> TYPE: PRT
<213> ORGANISM: Artificial Sequence
<220> FEATURE:
<223> OTHER INFORMATION: CPP sequence of the FHV Coat (amino acids
      35-49)

<400> SEQUENCE: 16

Arg Arg Arg Arg Asn Arg Thr Arg Arg Asn Arg Arg Arg Val Arg
1               5                   10                  15

<210> SEQ ID NO 17
<211> LENGTH: 19
<212> TYPE: PRT
<213> ORGANISM: Artificial Sequence
<220> FEATURE:
<223> OTHER INFORMATION: CPP sequence of BMV Gag (amino acids 7-25)

<400> SEQUENCE: 17

Lys Met Thr Arg Ala Gln Arg Arg Ala Ala Ala Arg Arg Asn Arg Trp
1               5                   10                  15

Thr Ala Arg

<210> SEQ ID NO 18
<211> LENGTH: 13
<212> TYPE: PRT
<213> ORGANISM: Artificial Sequence
<220> FEATURE:
<223> OTHER INFORMATION: CPP sequence  of HTLV-II Rex (amino acids 4-16)

<400> SEQUENCE: 18

Thr Arg Arg Gln Arg Thr Arg Arg Ala Arg Arg Asn Arg
1               5                   10
```

```
<210> SEQ ID NO 19
<211> LENGTH: 13
<212> TYPE: PRT
<213> ORGANISM: Artificial Sequence
<220> FEATURE:
<223> OTHER INFORMATION: CPP sequence of D-Tat

<400> SEQUENCE: 19

Gly Arg Lys Lys Arg Arg Gln Arg Arg Arg Pro Pro Gln
1               5                   10

<210> SEQ ID NO 20
<211> LENGTH: 13
<212> TYPE: PRT
<213> ORGANISM: Artificial Sequence
<220> FEATURE:
<223> OTHER INFORMATION: CPP sequence of R9-Tat

<400> SEQUENCE: 20

Gly Arg Arg Arg Arg Arg Arg Arg Arg Arg Pro Pro Gln
1               5                   10

<210> SEQ ID NO 21
<211> LENGTH: 17
<212> TYPE: PRT
<213> ORGANISM: Artificial Sequence
<220> FEATURE:
<223> OTHER INFORMATION: CPP sequence of MAP

<400> SEQUENCE: 21

Lys Leu Ala Leu Lys Leu Ala Leu Lys Leu Ala Leu Ala Leu Lys Leu
1               5                   10                  15

Ala

<210> SEQ ID NO 22
<211> LENGTH: 27
<212> TYPE: PRT
<213> ORGANISM: Artificial Sequence
<220> FEATURE:
<223> OTHER INFORMATION: CPP sequence of SBP

<400> SEQUENCE: 22

Met Gly Leu Gly Leu His Leu Leu Val Leu Ala Ala Ala Leu Gln Gly
1               5                   10                  15

Ala Trp Ser Gln Pro Lys Lys Lys Arg Lys Val
            20                  25

<210> SEQ ID NO 23
<211> LENGTH: 27
<212> TYPE: PRT
<213> ORGANISM: Artificial Sequence
<220> FEATURE:
<223> OTHER INFORMATION: CPP sequence of FBP

<400> SEQUENCE: 23

Gly Ala Leu Phe Leu Gly Trp Leu Gly Ala Ala Gly Ser Thr Met Gly
1               5                   10                  15

Ala Trp Ser Gln Pro Lys Lys Lys Arg Lys Val
            20                  25

<210> SEQ ID NO 24
<211> LENGTH: 27
<212> TYPE: PRT
<213> ORGANISM: Artificial Sequence
<220> FEATURE:
<223> OTHER INFORMATION: CPP sequence of MPG
```

-continued

<400> SEQUENCE: 24

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 25
<211> LENGTH: 27
<212> TYPE: PRT
<213> ORGANISM: Artificial Sequence
<220> FEATURE:
<223> OTHER INFORMATION: CPP sequence of MPG(ENLS)

<400> SEQUENCE: 25

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
            20                  25

<210> SEQ ID NO 26
<211> LENGTH: 21
<212> TYPE: PRT
<213> ORGANISM: Artificial Sequence
<220> FEATURE:
<223> OTHER INFORMATION: CPP sequence of Pep-1

<400> SEQUENCE: 26

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 27
<211> LENGTH: 21
<212> TYPE: PRT
<213> ORGANISM: Artificial Sequence
<220> FEATURE:
<223> OTHER INFORMATION: CPP sequence of Pep-2

<400> SEQUENCE: 27

Lys Glu Thr Trp Phe Glu Thr Trp Phe Thr Glu Trp Ser Gln Pro Lys
1               5                   10                  15

Lys Lys Arg Lys Val
            20

<210> SEQ ID NO 28
<211> LENGTH: 10
<212> TYPE: PRT
<213> ORGANISM: Artificial Sequence
<220> FEATURE:
<223> OTHER INFORMATION: CPP sequence

<400> SEQUENCE: 28

Gly Arg Lys Lys Arg Arg Gln Arg Arg Arg
1               5                   10

<210> SEQ ID NO 29
<211> LENGTH: 8
<212> TYPE: PRT
<213> ORGANISM: Artificial Sequence
<220> FEATURE:
<223> OTHER INFORMATION: CPP sequence

<400> SEQUENCE: 29

```
Arg Arg Arg Arg Arg Arg Leu Arg
1               5
```

<210> SEQ ID NO 30
<211> LENGTH: 12
<212> TYPE: PRT
<213> ORGANISM: Artificial Sequence
<220> FEATURE:
<223> OTHER INFORMATION: CPP sequence

<400> SEQUENCE: 30

```
Arg Arg Gln Arg Arg Thr Ser Lys Leu Met Lys Arg
1               5                   10
```

<210> SEQ ID NO 31
<211> LENGTH: 27
<212> TYPE: PRT
<213> ORGANISM: Artificial Sequence
<220> FEATURE:
<223> OTHER INFORMATION: Transportan peptide

<400> SEQUENCE: 31

```
Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25
```

<210> SEQ ID NO 32
<211> LENGTH: 33
<212> TYPE: PRT
<213> ORGANISM: Artificial Sequence
<220> FEATURE:
<223> OTHER INFORMATION: CPP sequence

<400> SEQUENCE: 32

```
Lys Ala Leu Ala Trp Glu Ala Lys Leu Ala Lys Ala Leu Ala Lys Ala
1               5                   10                  15

Leu Ala Lys His Leu Ala Lys Ala Leu Ala Lys Ala Leu Lys Cys Glu
            20                  25                  30

Ala
```

<210> SEQ ID NO 33
<211> LENGTH: 16
<212> TYPE: PRT
<213> ORGANISM: Artificial Sequence
<220> FEATURE:
<223> OTHER INFORMATION: CPP sequence

<400> SEQUENCE: 33

```
Arg Gln Ile Lys Ile Trp Phe Gln Asn Arg Arg Met Lys Trp Lys Lys
1               5                   10                  15
```

<210> SEQ ID NO 34
<211> LENGTH: 11
<212> TYPE: PRT
<213> ORGANISM: Artificial Sequence
<220> FEATURE:
<223> OTHER INFORMATION: CPP sequence

<400> SEQUENCE: 34

```
Tyr Gly Arg Lys Lys Arg Arg Gln Arg Arg Arg
1               5                   10
```

<210> SEQ ID NO 35

<211> LENGTH: 8
<212> TYPE: PRT
<213> ORGANISM: Artificial Sequence
<220> FEATURE:
<223> OTHER INFORMATION: CPP sequence

<400> SEQUENCE: 35

Arg Lys Lys Arg Arg Gln Arg Arg
1               5

<210> SEQ ID NO 36
<211> LENGTH: 11
<212> TYPE: PRT
<213> ORGANISM: Artificial Sequence
<220> FEATURE:
<223> OTHER INFORMATION: CPP sequence

<400> SEQUENCE: 36

Tyr Ala Arg Ala Ala Ala Arg Gln Ala Arg Ala
1               5                   10

<210> SEQ ID NO 37
<211> LENGTH: 11
<212> TYPE: PRT
<213> ORGANISM: Artificial Sequence
<220> FEATURE:
<223> OTHER INFORMATION: CPP sequence

<400> SEQUENCE: 37

Thr His Arg Leu Pro Arg Arg Arg Arg Arg Arg
1               5                   10

<210> SEQ ID NO 38
<211> LENGTH: 11
<212> TYPE: PRT
<213> ORGANISM: Artificial Sequence
<220> FEATURE:
<223> OTHER INFORMATION: CPP sequence

<400> SEQUENCE: 38

Gly Gly Arg Arg Ala Arg Arg Arg Arg Arg Arg
1               5                   10

<210> SEQ ID NO 39
<211> LENGTH: 7
<212> TYPE: PRT
<213> ORGANISM: Artificial Sequence
<220> FEATURE:
<223> OTHER INFORMATION: NLS sequence of SV40 large T Antigen

<400> SEQUENCE: 39

Pro Lys Lys Lys Arg Lys Val
1               5

<210> SEQ ID NO 40
<211> LENGTH: 16
<212> TYPE: PRT
<213> ORGANISM: Artificial Sequence
<220> FEATURE:
<223> OTHER INFORMATION: NLS sequence of Nucleoplasmin

<400> SEQUENCE: 40

Lys Arg Pro Ala Ala Ile Lys Lys Ala Gly Gln Ala Lys Lys Lys Lys
1               5                   10                  15

<210> SEQ ID NO 41
<211> LENGTH: 18

-continued

```
<212> TYPE: PRT
<213> ORGANISM: Artificial Sequence
<220> FEATURE:
<223> OTHER INFORMATION: NLS sequence of CBP80

<400> SEQUENCE: 41

Arg Arg Arg His Ser Asp Glu Asn Asp Gly Gly Gln Pro His Lys Arg
1               5                   10                  15

Arg Lys

<210> SEQ ID NO 42
<211> LENGTH: 11
<212> TYPE: PRT
<213> ORGANISM: Artificial Sequence
<220> FEATURE:
<223> OTHER INFORMATION: NLS sequence of HIV-I Rev protein

<400> SEQUENCE: 42

Arg Gln Ala Arg Arg Asn Arg Arg Arg Trp Glu
1               5                   10

<210> SEQ ID NO 43
<211> LENGTH: 18
<212> TYPE: PRT
<213> ORGANISM: Artificial Sequence
<220> FEATURE:
<223> OTHER INFORMATION: NLS sequence of HTLV-I Rex

<400> SEQUENCE: 43

Met Pro Lys Thr Arg Arg Arg Pro Arg Arg Ser Gln Arg Lys Arg Pro
1               5                   10                  15

Pro Thr

<210> SEQ ID NO 44
<211> LENGTH: 37
<212> TYPE: PRT
<213> ORGANISM: Artificial Sequence
<220> FEATURE:
<223> OTHER INFORMATION: NLS of hnRNP A

<400> SEQUENCE: 44

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Lys Pro Arg
                20                  25                  30

Asn Gln Gly Gly Tyr
            35

<210> SEQ ID NO 45
<211> LENGTH: 43
<212> TYPE: PRT
<213> ORGANISM: Artificial Sequence
<220> FEATURE:
<223> OTHER INFORMATION: NLS of rpL23a

<400> SEQUENCE: 45

Val His Ser His Lys Lys Lys Lys Ile Arg Thr Ser Pro Thr Phe Thr
1               5                   10                  15

Thr Pro Lys Thr Leu Arg Leu Arg Arg Gln Pro Lys Tyr Pro Arg Lys
                20                  25                  30

Ser Ala Pro Arg Arg Asn Lys Leu Asp His Tyr
            35                  40
```

```
<210> SEQ ID NO 46
<211> LENGTH: 4
<212> TYPE: PRT
<213> ORGANISM: Artificial Sequence
<220> FEATURE:
<223> OTHER INFORMATION: NLS sequence
<220> FEATURE:
<221> NAME/KEY: VARIANT
<222> LOCATION: (2)..(2)
<223> OTHER INFORMATION: /replace="R or K"
<220> FEATURE:
<221> NAME/KEY: MISC_FEATURE
<222> LOCATION: (3)..(3)
<223> OTHER INFORMATION: Xaa can be any naturally occurring amino acid
<220> FEATURE:
<221> NAME/KEY: VARIANT
<222> LOCATION: (4)..(4)
<223> OTHER INFORMATION: /replace="R or K"

<400> SEQUENCE: 46

Lys Xaa Xaa Xaa
1

<210> SEQ ID NO 47
<211> LENGTH: 101
<212> TYPE: PRT
<213> ORGANISM: Artificial Sequence
<220> FEATURE:
<223> OTHER INFORMATION: OMOMYC TAT

<400> SEQUENCE: 47

Met Thr Glu Glu Asn Val Lys Arg Arg Thr His Asn Val Leu Glu Arg
1               5                   10                  15

Gln Arg Arg Asn Glu Leu Lys Arg Ser Phe Phe Ala Leu Arg Asp Gln
            20                  25                  30

Ile Pro Glu Leu Glu Asn Asn Glu Lys Ala Pro Lys Val Val Ile Leu
        35                  40                  45

Lys Lys Ala Thr Ala Tyr Ile Leu Ser Val Gln Ala Glu Thr Gln Lys
    50                  55                  60

Leu Ile Ser Glu Ile Asp Leu Leu Arg Lys Gln Asn Glu Gln Leu Lys
65                  70                  75                  80

His Lys Leu Glu Gln Leu Arg Asn Ser Cys Ala Gly Arg Lys Lys Arg
                85                  90                  95

Arg Gln Arg Arg Arg
            100

<210> SEQ ID NO 48
<211> LENGTH: 99
<212> TYPE: PRT
<213> ORGANISM: Artificial Sequence
<220> FEATURE:
<223> OTHER INFORMATION: OMOMYC LZArg

<400> SEQUENCE: 48

Met Thr Glu Glu Asn Val Lys Arg Arg Thr His Asn Val Leu Glu Arg
1               5                   10                  15

Gln Arg Arg Asn Glu Leu Lys Arg Ser Phe Phe Ala Leu Arg Asp Gln
            20                  25                  30

Ile Pro Glu Leu Glu Asn Asn Glu Lys Ala Pro Lys Val Val Ile Leu
        35                  40                  45

Lys Lys Ala Thr Ala Tyr Ile Leu Ser Val Gln Ala Glu Thr Gln Lys
    50                  55                  60

Leu Ile Ser Glu Ile Asp Leu Leu Arg Lys Gln Asn Glu Gln Leu Lys
65                  70                  75                  80
```

His Lys Leu Glu Gln Leu Arg Asn Ser Cys Ala Arg Arg Arg Arg
                85                  90                  95

Arg Leu Arg

<210> SEQ ID NO 49
<211> LENGTH: 11
<212> TYPE: PRT
<213> ORGANISM: Artificial Sequence
<220> FEATURE:
<223> OTHER INFORMATION: M2 domain

<400> SEQUENCE: 49

Arg Gln Arg Arg Asn Glu Leu Lys Arg Ser Phe
1               5                   10

<210> SEQ ID NO 50
<211> LENGTH: 9
<212> TYPE: PRT
<213> ORGANISM: Artificial Sequence
<220> FEATURE:
<223> OTHER INFORMATION: M1 peptide

<400> SEQUENCE: 50

Pro Ala Ala Lys Arg Val Lys Leu Asp
1               5

<210> SEQ ID NO 51
<211> LENGTH: 6
<212> TYPE: PRT
<213> ORGANISM: Artificial Sequence
<220> FEATURE:
<223> OTHER INFORMATION: peptide linker

<400> SEQUENCE: 51

Gly Pro Arg Arg Arg Arg
1               5

<210> SEQ ID NO 52
<211> LENGTH: 8
<212> TYPE: PRT
<213> ORGANISM: Artificial Sequence
<220> FEATURE:
<223> OTHER INFORMATION: Flag tag

<400> SEQUENCE: 52

Asp Tyr Lys Asp Asp Asp Asp Lys
1               5

<210> SEQ ID NO 53
<211> LENGTH: 8
<212> TYPE: PRT
<213> ORGANISM: Artificial Sequence
<220> FEATURE:
<223> OTHER INFORMATION: Strep tag

<400> SEQUENCE: 53

Trp Ser His Pro Gln Phe Glu Lys
1               5

<210> SEQ ID NO 54
<211> LENGTH: 9
<212> TYPE: PRT
<213> ORGANISM: Artificial Sequence
<220> FEATURE:
<223> OTHER INFORMATION: HA tag

```
<400> SEQUENCE: 54

Tyr Pro Tyr Asp Val Pro Asp Tyr Ala
1               5

<210> SEQ ID NO 55
<211> LENGTH: 14
<212> TYPE: PRT
<213> ORGANISM: Artificial Sequence
<220> FEATURE:
<223> OTHER INFORMATION: V5 tag

<400> SEQUENCE: 55

Gly Lys Pro Ile Pro Asn Pro Leu Leu Gly Leu Asp Ser Thr
1               5                   10

<210> SEQ ID NO 56
<211> LENGTH: 6
<212> TYPE: PRT
<213> ORGANISM: Artificial Sequence
<220> FEATURE:
<223> OTHER INFORMATION: peptide tag

<400> SEQUENCE: 56

Ala His Gly His Arg Pro
1               5

<210> SEQ ID NO 57
<211> LENGTH: 21
<212> TYPE: PRT
<213> ORGANISM: Artificial Sequence
<220> FEATURE:
<223> OTHER INFORMATION: peptide tag
<220> FEATURE:
<221> NAME/KEY: MISC_FEATURE
<222> LOCATION: (19)..(20)
<223> OTHER INFORMATION: Xaa can be any naturally occuring amino acid
<220> FEATURE:
<221> NAME/KEY: MISC_FEATURE
<222> LOCATION: (19)..(20)
<223> OTHER INFORMATION: Xaa can be any naturally occurring amino acid

<400> SEQUENCE: 57

Pro Ile His Asp His Asp His Pro His Leu Val Ile His Ser Gly Met
1               5                   10                  15

Thr Cys Xaa Xaa Cys
            20
```